(12) United States Patent
Urbalejo

(10) Patent No.: US 9,757,072 B1
(45) Date of Patent: Sep. 12, 2017

(54) WAVEFORM MARKER PLACEMENT ALGORITHM FOR USE IN NEUROPHYSIOLOGIC MONITORING

(71) Applicant: NuVasive, Inc., San Diego, CA (US)

(72) Inventor: Edward C Urbalejo, Carlsbad, CA (US)

(73) Assignee: NuVasive, Inc., San Diego, CA (US)

( * ) Notice: Subject to any disclaimer, the term of this patent is extended or adjusted under 35 U.S.C. 154(b) by 76 days.

(21) Appl. No.: 14/178,176

(22) Filed: Feb. 11, 2014

Related U.S. Application Data

(60) Provisional application No. 61/763,293, filed on Feb. 11, 2013.

(51) Int. Cl.
| | | |
|---|---|---|
| *A61B 5/04* | (2006.01) | |
| *A61B 5/00* | (2006.01) | |
| *A61N 1/04* | (2006.01) | |

(52) U.S. Cl.
CPC ........ *A61B 5/7235* (2013.01); *A61B 5/04001* (2013.01); *A61B 5/40* (2013.01); *A61N 1/0456* (2013.01)

(58) Field of Classification Search
CPC .................................................. A61B 5/7235
USPC ........................................................ 600/554
See application file for complete search history.

(56) References Cited

U.S. PATENT DOCUMENTS

| | | |
|---|---|---|
| 208,227 A | 9/1878 | Dorr |
| 972,983 A | 10/1910 | Arthur |
| 1,328,624 A | 1/1920 | Graham |
| 1,548,184 A | 8/1925 | Cameron |
| 2,704,064 A | 3/1955 | Fizzell et al. |
| 2,736,002 A | 2/1956 | Oriel |
| 2,808,826 A | 10/1957 | Reiner et al. |
| 3,364,929 A | 1/1968 | Ide et al. |
| 3,664,329 A | 5/1972 | Naylor |
| 3,682,162 A | 8/1972 | Colyer |
| 3,785,368 A | 1/1974 | McCarthy et al. |
| 3,830,226 A | 8/1974 | Staub |
| 3,851,641 A | 12/1974 | Toole et al. |
| 3,957,036 A | 5/1976 | Norman |
| 4,099,519 A | 7/1978 | Warren |
| 4,164,214 A | 8/1979 | Stark et al. |
| 4,207,897 A | 6/1980 | Lloyd et al. |
| 4,224,949 A | 9/1980 | Scott et al. |
| 4,226,228 A | 10/1980 | Shin et al. |
| 4,235,242 A | 11/1980 | Howson et al. |
| 4,252,130 A | 2/1981 | Le Pivert |

(Continued)

FOREIGN PATENT DOCUMENTS

WO    WO 2010044880 A1 *  4/2010  ........... A61B 5/0484

OTHER PUBLICATIONS

"Neurovision SE Nerve Locator/Monitor," RLN Systems Inc. Operator's Manual, 1999, 22 pages.

(Continued)

*Primary Examiner* — Michael C Stout
*Assistant Examiner* — Nicholas E Kolderman
(74) *Attorney, Agent, or Firm* — Stephen H. Hall; Michael L. Williams; Bradley Arant Boult Cummings LLP

(57) ABSTRACT

The present invention relates to a system and methods generally aimed at surgery. More particularly, the present invention is directed at a system and related methods for performing surgical procedures and assessments involving the use of neurophysiology.

15 Claims, 31 Drawing Sheets

(56) References Cited

U.S. PATENT DOCUMENTS

| | | |
|---|---|---|
| 4,285,347 A | 8/1981 | Hess |
| 4,291,705 A | 9/1981 | Severinghaus et al. |
| 4,461,300 A | 7/1984 | Christensen |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,018 A | 6/1986 | Rantala |
| 4,633,889 A | 1/1987 | Talalla et al. |
| 4,658,835 A | 4/1987 | Pohndorf |
| 4,744,371 A | 5/1988 | Harris |
| 4,759,377 A | 7/1988 | Dykstra |
| 4,784,150 A | 11/1988 | Voorhies et al. |
| 4,807,642 A | 2/1989 | Brown |
| 4,892,105 A | 1/1990 | Prass |
| 4,926,865 A | 5/1990 | Oman |
| 4,962,766 A | 10/1990 | Herzon |
| 4,964,411 A | 10/1990 | Johnson et al. |
| 5,007,902 A | 4/1991 | Witt |
| 5,058,602 A | 10/1991 | Brody |
| 5,081,990 A | 1/1992 | Deletis |
| 5,092,344 A | 3/1992 | Lee |
| 5,127,403 A | 7/1992 | Brownlee |
| 5,161,533 A | 11/1992 | Prass et al. |
| 5,196,015 A | 3/1993 | Neubardt |
| 5,220,920 A | 6/1993 | Gharib |
| RE34,390 E | 9/1993 | Culver |
| 5,255,691 A | 10/1993 | Otten |
| 5,282,468 A | 2/1994 | Klepinski |
| 5,284,153 A | 2/1994 | Raymond et al. |
| 5,284,154 A | 2/1994 | Raymond et al. |
| 5,299,563 A | 4/1994 | Seton |
| 5,312,417 A | 5/1994 | Wilk |
| 5,313,956 A | 5/1994 | Knutsson et al. |
| 5,327,902 A | 7/1994 | Lemmen |
| 5,333,618 A | 8/1994 | Lekhtman et al. |
| 5,375,067 A | 12/1994 | Berchin |
| 5,383,876 A | 1/1995 | Nardella |
| 5,450,845 A | 9/1995 | Axelgaard |
| 5,474,558 A | 12/1995 | Neubardt |
| 5,480,440 A | 1/1996 | Kambin |
| 5,482,038 A | 1/1996 | Ruff |
| 5,484,437 A | 1/1996 | Michelson |
| 5,540,235 A | 7/1996 | Wilson |
| 5,549,656 A | 8/1996 | Reiss |
| 5,560,372 A | 10/1996 | Cory |
| 5,566,678 A | 10/1996 | Cadwell |
| 5,579,781 A | 12/1996 | Cooke |
| 5,593,429 A | 1/1997 | Ruff |
| 5,599,279 A | 2/1997 | Slotman |
| 5,601,608 A | 2/1997 | Mouchawar |
| 5,630,813 A | 5/1997 | Kieturakis |
| 5,671,752 A | 9/1997 | Sinderby et al. |
| 5,707,359 A | 1/1998 | Bufalini |
| 5,711,307 A | 1/1998 | Smits |
| 5,728,046 A | 3/1998 | Mayer |
| 5,741,253 A | 4/1998 | Michelson |
| 5,758,643 A | 6/1998 | Wong et al. |
| 5,759,159 A | 6/1998 | Masreliez |
| 5,772,661 A | 6/1998 | Michelson |
| 5,775,331 A | 7/1998 | Raymond et al. |
| 5,776,144 A | 7/1998 | Leysieffer et al. |
| 5,779,642 A | 7/1998 | Nightengale |
| 5,785,658 A | 7/1998 | Benaron et al. |
| 5,797,854 A | 8/1998 | Hedgecock |
| 5,806,522 A | 9/1998 | Katims |
| 5,807,272 A | 9/1998 | Kun et al. |
| 5,814,073 A | 9/1998 | Bonutti |
| 5,830,151 A | 11/1998 | Hadzic et al. |
| 5,851,191 A | 12/1998 | Gozani et al. |
| 5,853,373 A | 12/1998 | Griffith et al. |
| 5,860,973 A | 1/1999 | Michelson |
| 5,862,314 A | 1/1999 | Jeddeloh |
| 5,872,314 A | 2/1999 | Clinton |
| 5,885,219 A | 3/1999 | Nightengale |
| 5,888,196 A | 3/1999 | Bonutti |
| 5,902,231 A | 5/1999 | Foley et al. |
| 5,928,139 A | 7/1999 | Koros et al. |
| 5,928,158 A | 7/1999 | Aristides |
| 5,928,159 A | 7/1999 | Eggers et al. |
| 5,935,131 A | 8/1999 | Bonutti |
| 5,938,688 A | 8/1999 | Schiff |
| 5,947,964 A | 9/1999 | Eggers et al. |
| 5,976,094 A | 11/1999 | Gozani |
| 6,004,262 A | 12/1999 | Putz et al. |
| 6,011,985 A | 1/2000 | Athan |
| 6,026,323 A | 2/2000 | Skladnev et al. |
| 6,027,456 A | 2/2000 | Feler et al. |
| 6,038,469 A | 3/2000 | Karlsson et al. |
| 6,038,477 A | 3/2000 | Kayyali |
| 6,050,992 A | 4/2000 | Nichols |
| 6,074,343 A | 6/2000 | Nathanson et al. |
| 6,104,957 A | 8/2000 | Alo et al. |
| 6,104,960 A | 8/2000 | Duysens et al. |
| 6,119,068 A | 9/2000 | Kannonji |
| 6,120,503 A | 9/2000 | Michelson |
| 6,128,576 A | 10/2000 | Nishimoto |
| 6,132,386 A | 10/2000 | Gozani et al. |
| 6,132,387 A | 10/2000 | Gozani et al. |
| 6,135,965 A | 10/2000 | Turner et al. |
| 6,139,493 A | 10/2000 | Koros et al. |
| 6,146,335 A | 11/2000 | Gozani |
| 6,161,047 A | 12/2000 | King et al. |
| 6,181,961 B1 | 1/2001 | Prass |
| 6,206,826 B1 | 3/2001 | Mathews et al. |
| 6,224,549 B1 * | 5/2001 | Drongelen ............. 600/300 |
| 6,259,945 B1 | 7/2001 | Epstein et al. |
| 6,266,558 B1 | 7/2001 | Gozani et al. |
| 6,273,905 B1 | 8/2001 | Streeter |
| 6,292,701 B1 | 9/2001 | Prass et al. |
| 6,306,100 B1 | 10/2001 | Prass |
| 6,312,392 B1 | 11/2001 | Herzon |
| 6,325,764 B1 | 12/2001 | Griffith et al. |
| 6,334,068 B1 | 12/2001 | Hacker |
| 6,337,994 B1 | 1/2002 | Stoianovici et al. |
| 6,393,325 B1 | 5/2002 | Mann et al. |
| 6,407,335 B1 | 6/2002 | Franklin-Lees et al. |
| 6,425,859 B1 | 7/2002 | Foley et al. |
| 6,425,901 B1 | 7/2002 | Zhu et al. |
| 6,451,015 B1 | 9/2002 | Rittman et al. |
| 6,466,817 B1 | 10/2002 | Kaula et al. |
| 6,500,128 B2 | 12/2002 | Marino |
| 6,535,759 B1 | 3/2003 | Epstein et al. |
| 6,564,078 B1 | 5/2003 | Marino et al. |
| 6,579,244 B2 | 6/2003 | Goodwin |
| 6,593,528 B2 | 7/2003 | Franklin-Lees et al. |
| 6,719,692 B2 | 4/2004 | Kleffner et al. |
| 6,760,616 B2 | 7/2004 | Hoey et al. |
| 6,796,985 B2 | 9/2004 | Bolger et al. |
| 6,819,956 B2 | 11/2004 | DiLorenzo |
| 6,829,508 B2 | 12/2004 | Schulman et al. |
| 6,849,047 B2 | 2/2005 | Goodwin |
| 6,855,105 B2 | 2/2005 | Jackson, III |
| 6,902,569 B2 | 6/2005 | Parmer et al. |
| 6,926,728 B2 | 8/2005 | Zucherman et al. |
| 6,929,606 B2 | 8/2005 | Ritland |
| 7,047,082 B1 | 5/2006 | Schrom et al. |
| 7,050,848 B2 | 5/2006 | Hoey et al. |
| 7,079,883 B2 | 7/2006 | Marino et al. |
| 7,089,059 B1 | 8/2006 | Pless |
| D533,875 S | 12/2006 | Miles et al. |
| 7,177,677 B2 | 2/2007 | Kaula et al. |
| 7,207,949 B2 | 4/2007 | Miles et al. |
| 7,255,680 B2 | 8/2007 | Gharib |
| 7,470,236 B1 | 12/2008 | Kelleher et al. |
| 7,522,953 B2 | 4/2009 | Kaula et al. |
| 7,582,058 B1 | 9/2009 | Miles et al. |
| 7,657,308 B2 | 2/2010 | Miles et al. |
| 7,664,544 B2 | 2/2010 | Miles et al. |
| 7,691,057 B2 | 4/2010 | Miles et al. |
| 7,706,843 B2 | 4/2010 | Kaplan |

(56) References Cited

U.S. PATENT DOCUMENTS

| | | |
|---|---|---|
| 7,819,801 B2 | 10/2010 | Miles et al. |
| 7,857,813 B2 | 12/2010 | Schmitz et al. |
| 7,878,981 B2 | 2/2011 | Strother et al. |
| 7,887,538 B2 | 2/2011 | Bleich et al. |
| 7,896,815 B2 | 3/2011 | Thrope et al. |
| 7,905,840 B2 | 3/2011 | Pimenta et al. |
| 7,938,830 B2 | 5/2011 | Saadat et al. |
| 7,963,927 B2 | 6/2011 | Kelleher et al. |
| 8,068,912 B2 | 11/2011 | Kaula et al. |
| 8,255,045 B2 | 8/2012 | Gharib et al. |
| 2001/0039949 A1 | 11/2001 | Loubser |
| 2001/0056280 A1 | 12/2001 | Underwood et al. |
| 2002/0007129 A1 | 1/2002 | Marino |
| 2002/0072686 A1 | 6/2002 | Hoey et al. |
| 2002/0123780 A1 | 9/2002 | Grill et al. |
| 2002/0134570 A1 | 9/2002 | Franklin-Lees et al. |
| 2002/0161415 A1 | 10/2002 | Cohen et al. |
| 2002/0193843 A1 | 12/2002 | Hill |
| 2003/0032966 A1 | 2/2003 | Foley et al. |
| 2003/0105503 A1 | 6/2003 | Marino |
| 2004/0199084 A1 | 10/2004 | Kelleher et al. |
| 2004/0203490 A1 | 10/2004 | Kaplan |
| 2004/0225228 A1 | 11/2004 | Ferree |
| 2005/0004593 A1 | 1/2005 | Simonson |
| 2005/0004623 A1 | 1/2005 | Miles et al. |
| 2005/0033380 A1 | 2/2005 | Tanner et al. |
| 2005/0075578 A1 | 4/2005 | Gharib et al. |
| 2005/0149035 A1 | 7/2005 | Pimenta et al. |
| 2005/0182454 A1 | 8/2005 | Gharib et al. |
| 2005/0192575 A1 | 9/2005 | Pacheco |
| 2006/0025703 A1* | 2/2006 | Miles .................. A61B 5/04001 600/554 |
| 2006/0052828 A1 | 3/2006 | Kim et al. |
| 2006/0069315 A1 | 3/2006 | Miles et al. |
| 2006/0224078 A1 | 10/2006 | Hoey et al. |
| 2007/0016097 A1 | 1/2007 | Farquhar et al. |
| 2007/0021682 A1 | 1/2007 | Gharib et al. |
| 2007/0198062 A1 | 8/2007 | Miles et al. |
| 2007/0293782 A1 | 12/2007 | Marino |
| 2008/0058606 A1 | 3/2008 | Miles et al. |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |
| 2008/0097164 A1 | 4/2008 | Miles et al. |
| 2008/0167574 A1 | 7/2008 | Farquhar et al. |
| 2008/0221473 A1 | 9/2008 | Calancie et al. |
| 2009/0018399 A1 | 1/2009 | Martinelli |
| 2009/0018610 A1 | 1/2009 | Gharib et al. |
| 2009/0054804 A1 | 2/2009 | Gharib et al. |
| 2009/0105604 A1 | 4/2009 | Bertagnoli et al. |
| 2009/0124860 A1 | 5/2009 | Miles et al. |
| 2009/0177112 A1 | 7/2009 | Gharib et al. |
| 2009/0192403 A1 | 7/2009 | Gharib et al. |
| 2009/0204016 A1 | 8/2009 | Gharib et al. |
| 2009/0204176 A1 | 8/2009 | Miles et al. |
| 2009/0209879 A1 | 8/2009 | Kaula et al. |
| 2009/0259108 A1 | 10/2009 | Miles et al. |
| 2010/0010367 A1 | 1/2010 | Foley et al. |
| 2010/0036384 A1 | 2/2010 | Gorek et al. |
| 2010/0069783 A1 | 3/2010 | Miles et al. |
| 2010/0076335 A1 | 3/2010 | Gharib et al. |
| 2010/0094093 A1 | 4/2010 | Miles et al. |
| 2010/0100001 A1* | 4/2010 | Aguilar .................. A61B 3/113 600/544 |
| 2010/0105986 A1 | 4/2010 | Miles et al. |
| 2010/0105987 A1 | 4/2010 | Miles et al. |
| 2010/0113884 A1 | 5/2010 | Miles et al. |
| 2010/0130827 A1 | 5/2010 | Pimenta et al. |
| 2010/0137690 A1 | 6/2010 | Miles et al. |
| 2010/0152603 A1 | 6/2010 | Miles et al. |
| 2010/0152604 A1 | 6/2010 | Kaula et al. |
| 2010/0160738 A1 | 6/2010 | Miles et al. |
| 2010/0174146 A1 | 7/2010 | Miles et al. |
| 2010/0174147 A1 | 7/2010 | Miles et al. |
| 2010/0174148 A1 | 7/2010 | Miles et al. |
| 2010/0249644 A1 | 9/2010 | Miles et al. |
| 2010/0273738 A1 | 10/2010 | Valcke et al. |
| 2010/0312103 A1 | 12/2010 | Gorek et al. |

OTHER PUBLICATIONS

Calancie et al., "Stimulus-Evoked EMG Monitoring During Transpedicular Lumbosacral Spine Instrumentation," *Spine*, 1994, 19(24): 2780-2786.

Holland et al., "Higher Electrical Stimulus Intensities are Required to Activate Chronically Compressed Nerve Roots. Implications for Intraoperative Electromyographic Pedicle Screw Testing," *Spine*, 1998, 23(2): 224-227.

* cited by examiner

US 9,757,072 B1

WAVEFORM MARKER PLACEMENT ALGORITHM FOR USE IN NEUROPHYSIOLOGIC MONITORING

CROSS-REFERENCE TO RELATED APPLICATIONS

This application is a utility patent application claiming the benefit of priority from commonly owned and U.S. Provisional Patent Application Ser. No. 61/763,293, entitled "Waveform Marker Placement Algorithm for Use in Neurophysiologic Monitoring," and filed on Feb. 11, 2013, the entire contents of which is hereby expressly incorporated by reference into this disclosure as if set forth in its entirety herein.

FIELD

The present invention relates to a system and methods generally aimed at surgery. More particularly, the present invention is directed at a system and related methods for performing surgical procedures and assessments involving the use of neurophysiologic recordings.

BACKGROUND

Neurophysiologic monitoring has become an increasingly important adjunct to surgical procedures where neural tissue may be at risk. Spinal surgery, in particular, involves working close to delicate tissue in and surrounding the spine, which can be damaged in any number of ways. Various neurophysiological techniques have been attempted and developed to monitor delicate nerve tissue during surgery in attempts to reduce the risk inherent in spine surgery (and surgery in general). Because of the complex structure of the spine and nervous system, no single monitoring technique has been developed that may adequately assess the risk to nervous tissue in all situations and complex techniques are often utilized in conjunction with one or more other complex monitoring techniques.

One such technique is somatosensory evoked potential (SSEP) monitoring which may be quite effective at detecting changes in the health of the dorsal column tracts of the spinal cord. SSEP (and other types of neurophysiologic monitoring) involves complex analysis and specially-trained neurophysiologists are often called upon to perform the monitoring. Even though performed by specialists, interpreting complex waveforms in this fashion is nonetheless disadvantageously time consuming, adding to the duration of the operation and translating into increased health care costs. For example, most neurophysiology systems require that a neurophysiologist visually identify the morphology of the SSEP responses, manually mark waveform amplitudes and latencies, and track those amplitude and latency values over time. Even more costly is the fact that the neurophysiologist is required in addition to the actual surgeon performing the spinal operation. The present invention is directed at eliminating, or at least reducing the effects of, the above-described problems with the prior art.

SUMMARY OF THE INVENTION

The present invention includes a system and methods for avoiding harm to neural tissue during surgery. According to a broad aspect, the present invention includes instruments capable of stimulating either the peripheral nerves of a patient, the spinal cord of a patient, or both, additional instruments capable of recording the evoked somatosensory responses, and a processing system. The instrument is configured to deliver a stimulation signal preoperatively, perioperatively, and postoperatively. The processing unit is further programmed to and measure the response of nerves depolarized by said stimulation signals as received by the somatosensory cortex to indicate spinal cord health.

According to another broad aspect, the present invention includes a control unit, a patient module, and a plurality of surgical accessories adapted to couple to the patient module. The control unit includes a power supply and is programmed to receive user commands, activate stimulation in a plurality of predetermined modes, process signal data according to defined algorithms, display received parameters and processed data, and monitor system status. The patient module is in communication with the control unit. The patient module is within the sterile field. The patient module includes signal conditioning circuitry, stimulator drive circuitry, and signal conditioning circuitry required to perform said stimulation in said predetermined modes. The patient module includes a processor programmed to perform a plurality of predetermined functions including at least two of static pedicle integrity testing, dynamic pedicle integrity testing, nerve proximity detection, neuromuscular pathway assessment, manual motor evoked potential monitoring, automatic motor evoked potential monitoring, manual somatosensory evoked potential monitoring, automatic motor evoked potential monitoring, non-evoked monitoring, and surgical navigation.

According to another broad aspect, the present invention includes a neurophysiologic waveform marker placement algorithm that takes a discrete SSEP response, isolates the waveform from the noise, and automatically places latency markers on the isolated neurophysiologic signal.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination. It is also expressly noted that, although described herein largely in terms of use in spinal surgery, the neuromonitoring system and related methods described herein are suitable for use in any number of additional procedures, surgical or otherwise, wherein assessing the health of the spinal cord and/or various other nerve tissue may prove beneficial. It is further expressly noted that, although described herein largely in terms of SSEP testing, the waveform marker placement algorithms described herein are suitable for use with any number of additional physiologic responses types, including but not limited to brainstem auditory evoked potentials (BAEPs).

Figure 1:
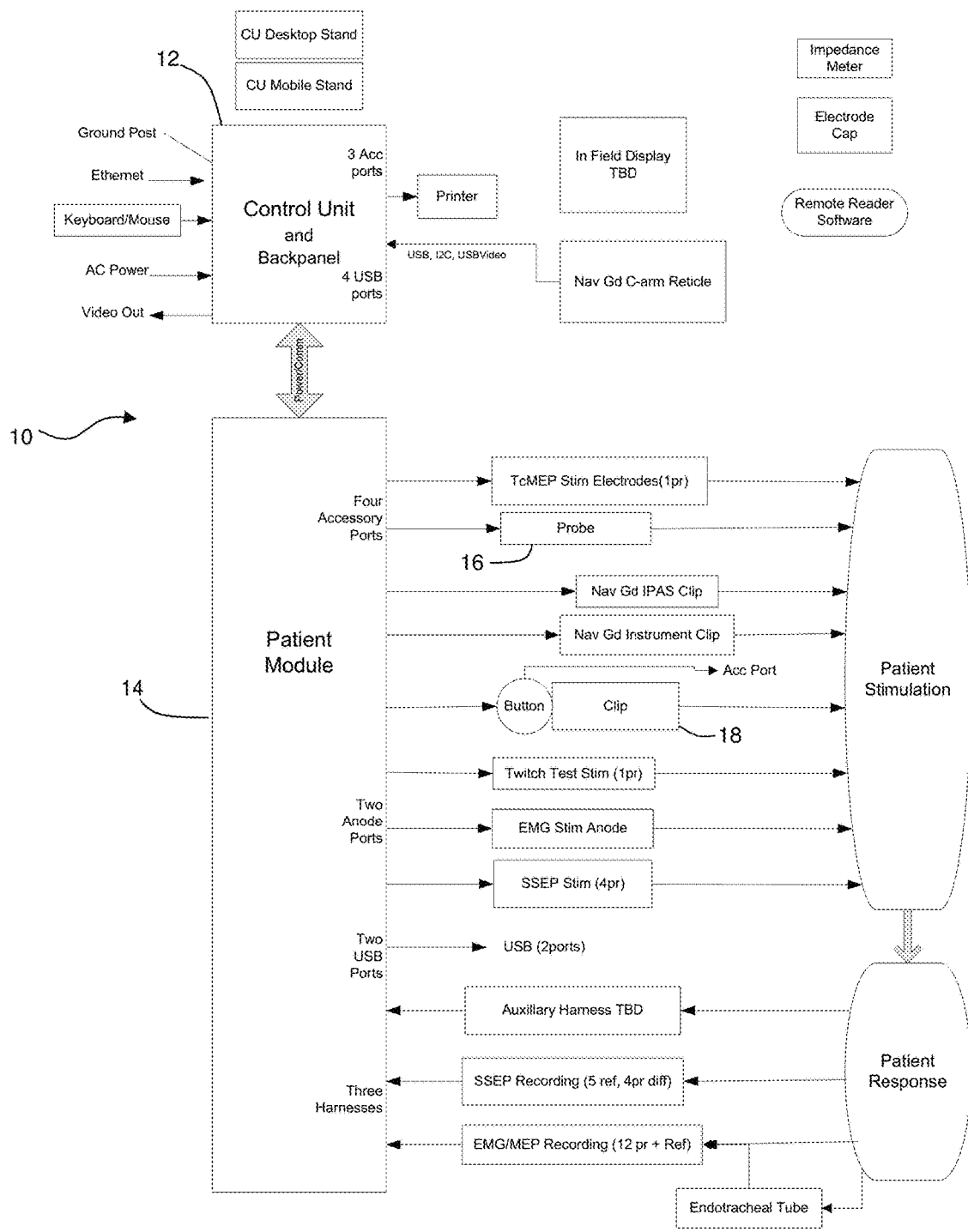
FIG. 1 is a block diagram of an example neurophysiology system capable of conducting multiple nerve and spinal cord monitoring functions including but not necessarily limited to SSEP Manual, SSEP Automatic, MEP Manual, MEP Automatic, neuromuscular pathway, bone integrity, nerve detection, and nerve pathology (evoked or free-run EMG) assessments.
Figure 2:
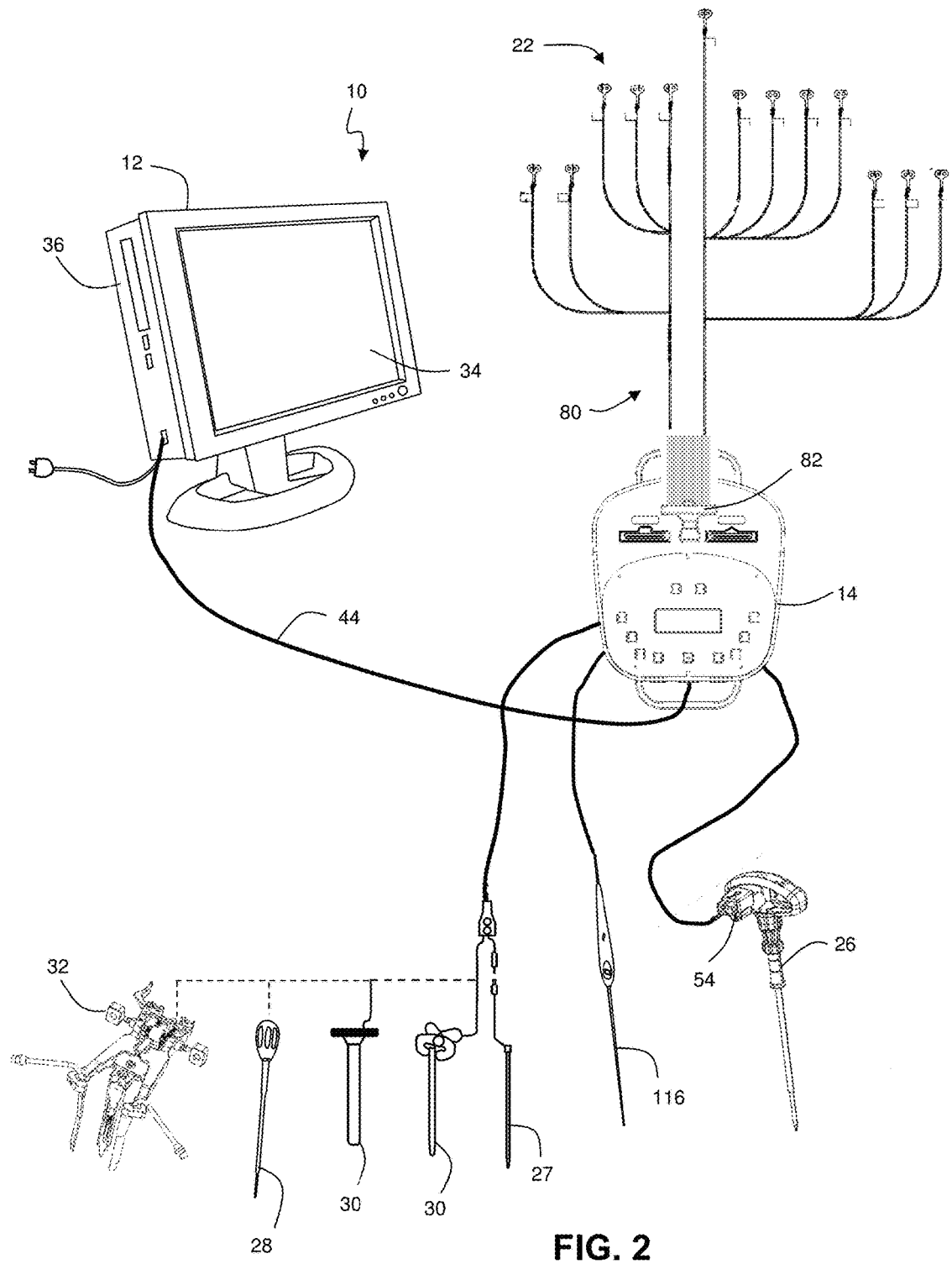
FIG. 2 is a perspective view showing examples of several components of the neurophysiology system of FIG. 1.

A neuromonitoring system 10 is described herein and is capable of performing a number of neurophysiological and/or guidance assessments at the direction of the surgeon (and/or other members of the surgical team). By way of example only, FIGS. 1-2 illustrate the basic components of the neurophysiology system 10. The system comprises a control unit 12 (including a main display 34 preferably equipped with a graphical user interface (GUI) and a processing unit 36 that collectively contain the essential processing capabilities for controlling the system 10), a patient module 14, a stimulation accessory (e.g. a stimulation probe 16, stimulation clip 18 for connection to various surgical instruments, an inline stimulation hub 20, and stimulation electrodes 22), and a plurality of recording electrodes 24 for detecting electrical potentials. The stimulation clip 18 may be used to connect any of a variety of surgical instruments to the system 10, including, but not necessarily limited to a pedicle access needle 26, k-wire 27, tap 28, dilator(s) 30, tissue retractor 32, etc. One or more secondary feedback devices (e.g. secondary display 46) may also be provided for additional expression of output to a user and/or receiving input from the user.

The functions performed by the neuromonitoring system 10 may include, but are not necessarily limited to, the Twitch Test, Free-run EMG, Basic Stimulated EMG, Dynamic Stimulated EMG, XLIF®, Nerve Retractor, MEP Manual, MEP Automatic, and SSEP Manual, SSEP Automatic, and Navigated Guidance modes, all of which will be described briefly below. The Twitch Test mode is designed to assess the neuromuscular pathway via the so-called "train-of-four test" to ensure the neuromuscular pathway is free from muscle relaxants prior to performing neurophysiology-based testing, such as bone integrity (e.g. pedicle) testing, nerve detection, and nerve retraction. This is described in greater detail within PCT Patent App. No. PCT/US2005/036089, entitled "System and Methods for Assessing the Neuromuscular Pathway Prior to Nerve Testing," filed Oct. 7, 2005, the entire contents of which is hereby incorporated by reference as if set forth fully herein. The Basic Stimulated EMG Dynamic Stimulated EMG tests are designed to assess the integrity of bone (e.g. pedicle) during all aspects of pilot hole formation (e.g., via an awl), pilot hole preparation (e.g. via a tap), and screw introduction (during and after). These modes are described in greater detail in PCT Patent App. No. PCT/US02/35047 entitled "System and Methods for Performing Percutaneous Pedicle Integrity Assessments," filed on Oct. 30, 2002, and PCT Patent App. No. PCT/US2004/025550, entitled "System and Methods for Performing Dynamic Pedicle Integrity Assessments," filed on Aug. 5, 2004 the entire contents of which are both hereby incorporated by reference as if set forth fully herein. The XLIF mode is designed to detect the presence of nerves during the use of the various surgical access instruments of the neuromonitoring system 10, including the pedicle access needle 26, k-wire 42, dilator 44, and retractor assembly 70. This mode is described in greater detail within PCT Patent App. No. PCT/US2002/22247, entitled "System and Methods for Determining Nerve Proximity, Direction, and Pathology During Surgery," filed on Jul. 11, 2002, the entire contents of which is hereby incorporated by reference as if set forth fully herein. The Nerve Retractor mode is designed to assess the health or pathology of a nerve before, during, and after retraction of the nerve during a surgical procedure. This mode is described in greater detail within PCT Patent App. No. PCT/US2002/30617, entitled "System and Methods for Performing Surgical Procedures and Assessments," filed on Sep. 25, 2002, the entire contents of which are hereby incorporated by reference as if set forth fully herein. The MEP Auto and MEP Manual modes are designed to test the motor pathway to detect potential damage to the spinal cord by stimulating the motor cortex in the brain and recording the resulting EMG response of various muscles in the upper and lower extremities. The SSEP function is designed to test the sensory pathway to detect potential damage to the spinal cord by stimulating peripheral nerves inferior to the target spinal level and recording the action potential from sensors superior to the spinal level. The MEP Auto, MEP manual, and SSEP modes are described in greater detail within PCT Patent App. No. PCT/US2006/003966, entitled "System and Methods for Performing Neurophysiologic Assessments During Spine Surgery," filed on Feb. 2, 2006, the entire contents of which is hereby incorporated by reference as if set forth fully herein. The SSEP Auto and SSEP Manual modes are described in greater detail within PCT Patent App. No. PCT/US/2009/05650, entitled "Neurophysiologic Monitoring System and Related Methods," filed on Oct. 15, 2008, the entire contents of which is hereby incorporated by reference as if set forth fully herein. The Navigated Guidance function is designed to facilitate the safe and reproducible use of surgical instruments and/or implants by providing the ability to determine the optimal or desired trajectory for surgical instruments and/or implants and monitor the trajectory of surgical instruments and/or implants during surgery. This mode is described in greater detail within PCT Patent App. No. PCT/US2007/11962, entitled "Surgical Trajectory Monitoring System and Related Methods," filed on Jul. 30, 2007, and PCT Patent App. No. PCT/US2008/12121, the entire contents of which are each incorporated herein by reference as if set forth fully herein. These functions will be explained now in brief detail.

Before further addressing the various functional modes of the neurophysiologic system 10, the hardware components and features of the system 10 will be describe in further detail. The control unit 12 of the neurophysiology system 10 includes a main display 34 and a processing unit 36, which collectively contain the essential processing capabilities for controlling the neurophysiology system 10. The main display 34 is preferably equipped with a graphical user interface (GUI) capable of graphically communicating information to the user and receiving instructions from the user. The processing unit 36 contains computer hardware and software that commands the stimulation source (e.g. patient module 14), receives digital and/or analog signals and other information from the patient module 14, processes SSEP response signals, and displays the processed data to the user via the display 34. The primary functions of the software within the control unit 12 include receiving user commands via the touch screen main display 34, activating stimulation in the appropriate mode (Basic Stimulated EMG, Dynamic Stimulated EMG, XLIF, MEP automatic, MEP manual, SSEP manual, SSEP auto, and Twitch Test), processing signal data according to defined algorithms, displaying received parameters and processed data, and monitoring system status. According to one example embodiment, the main display 34 may comprise a 15" LCD display equipped with suitable touch screen technology and the processing unit 36 may comprise a 2 GHz. The processing unit 36 further includes a powered USB port 38 for connection to the patient module 14, a media drive (e.g. CD, CD-RW, DVD, DVD-RW, etc. . . . ), a network port, wireless network card, and a plurality of additional ports 42 (e.g. USB, IEEE 1394, infrared, etc. . . . ) for attaching additional accessories, such as for example only, navigated guidance sensors, auxiliary stimulation anodes, and external devices (e.g. printer, keyboard, mouse, etc. . . . ). Preferably, during use the control unit 12 sits near the surgical table but outside the surgical field, such as for example, on a table top or a mobile stand. It will be appreciated, however, that if properly draped and protected, the control unit 12 may be located within the surgical (sterile) field.

The patient module 14 contains a digital communications interface to communicate with the control unit 12, as well as the electrical connections to all recording and stimulation electrodes, signal conditioning circuitry, stimulator drive and steering circuitry, and signal conditioning circuitry required to perform all of the functional modes of the neurophysiology system 10, including but not necessarily limited to Basic Stimulated EMG, Dynamic Stimulated EMG, XLIF®, Twitch Test, MEP Manual and MEP Automatic, and SSEP Manual and SSEP Automatic. In one example, the patient module 14 includes thirty-two recording channels and eleven stimulation channels. A display (e.g. an LCD screen) may be provided on the face of the patient module 14, and may be utilized for showing simple status readouts (for example, results of a power on test, the electrode harnesses attached, and impedance data, etc. . . . ) or more procedure related data (for example, a stimulation threshold result, current stimulation level, selected function, etc. . . . ). The patient module 14 may be positioned near the patient in the sterile field during surgery.

To connect the array of recording electrodes 24 and stimulation electrodes 22 utilized by the system 10, the patient module 14 also includes a plurality of electrode harness ports. To simplify setup of the system 10, all of the recording electrodes 24 and stimulation electrodes 22 that are required to perform one of the various functional modes (including a common electrode 23 providing a ground reference to pre-amplifiers in the patient module 14, and an anode electrode 25 providing a return path for the stimulation current) may be bundled together and provided in single electrode harness 80. Depending on the desired function or functions to be used during a particular procedure, different groupings of recoding electrodes 24 and stimulation electrodes 22 may be required. According to one embodiment (set forth by way of example only), the electrode harnesses 80 are designed such that the various electrodes may be positioned about the patient (and preferably labeled accordingly) as described in Table 1 for SSEP:

TABLE 1

| SSEP | | |
|---|---|---|
| Electrode Type | Electrode Placement | Spinal Level |
| Ground | Shoulder | — |
| Stimulation | Left Post Tibial Nerve | — |
| Stimulation | Left Ulnar Nerve | — |
| Stimulation | Right Post Tibial Nerve | — |
| Stimulation | Right Ulnar Nerve | — |
| Recording | Left Popliteal Fossa | — |
| Recording | Left Erb's Point | — |
| Recording | Left Scalp Cp3 | — |
| Recording | Right Popliteal Fossa | — |
| Recording | Right Erb's Point | — |
| Recording | Right Scalp Cp4 | — |
| Recording | Center Scalp Fpz | — |
| Recording | Center Scalp Cz | — |
| Recording | Center Cervical Spine | — |

Having described an example embodiment of the system 10 and the hardware components that comprise it, the neurophysiological functionality and methodology of the system 10 will now be described in further detail.

The neuromonitoring system 10 performs assessments of spinal cord health using one or more of SSEP Auto, and SSEP manual modes. In the SSEP modes, the neuromonitoring system 10 stimulates peripheral sensory nerves that exit the spinal cord below the level of surgery and then measures the electrical action potential from electrodes located on the nervous system superior to the surgical target site. Recording sites below the applicable target site are also preferably monitored as a positive control measure to ensure variances from normal or expected results are not due to problems with the stimulation signal deliver (e.g. misplaced stimulation electrode, inadequate stimulation signal parameters, etc.). To accomplish this, stimulation electrodes 22 may be placed on the skin over the desired peripheral nerve (such as by way of example only, the left and right Posterior Tibial nerve and/or the left and right Ulnar nerve) and recording electrodes 24 are positioned on the recording sites (such as, by way of example only, C2 vertebra, Cp3 scalp, Cp4 scalp, Erb's point, Popliteal Fossa) and stimulation signals are delivered from the patient module 14.

Damage in the spinal cord may disrupt the transmission of the signal up along the spinothalamic pathway through the spinal cord resulting in a weakened, delayed, or absent signal at the recording sites superior to the surgery location (e.g. cortical and subcortical sites). To check for these occurrences, the system 10 monitors the amplitude and latency of the evoked signal response. According to one embodiment, the system 10 may perform SSEP in either of two modes: Automatic mode and Manual mode. In SSEP Auto mode, the system 10 compares the difference between the amplitude and latency of the signal response vs. the amplitude and latency of a baseline signal response. The difference is compared against predetermined "safe" and "unsafe" levels and the results are displayed on display 34. According to one embodiment, the system may determine safe and unsafe levels based on each of the amplitude and latency values for each of the cortical and subcortical sites individually, for each stimulation channel. That is, if either of the subcortical and cortical amplitudes decrease by a predetermined level, or either of the subcortical and cortical latency values increase by a predetermined level, the system may issue a warning. By way of example, the alert may comprise a Red, Yellow, Green type warning associated with the applicable channel wherein Red indicates that at least one of the determined values falls within the unsafe level, the color green may indicate that all of the values fall within the safe level, and the color yellow may indicate that at least one of the values falls between the safe and unsafe levels. To generate more information, the system 10 may analyze the results in combination. With this information, in addition to the Red, Yellow, and Green alerts, the system 10 may indicate possible causes for the results achieved. In SSEP Manual mode, signal response waveforms and amplitude and latency values associated with those waveforms are displayed for the user. The user then makes the comparison between a baseline the signal response.

Figure 3:
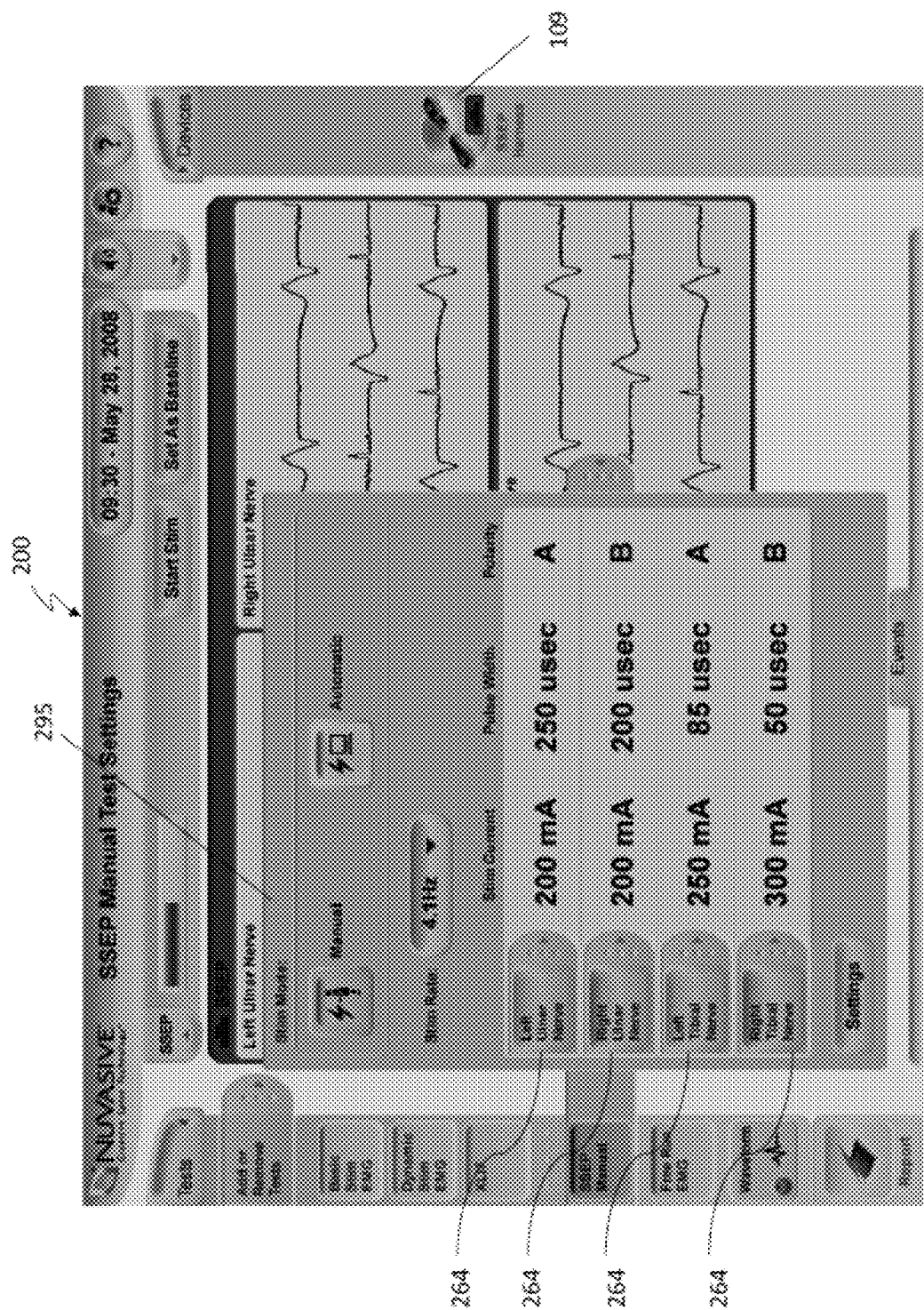
FIG. 3 is an exemplary screen display illustrating one embodiment of an SSEP profile selection screen forming part of the neurophysiology system of FIG. 1.
Figure 4:
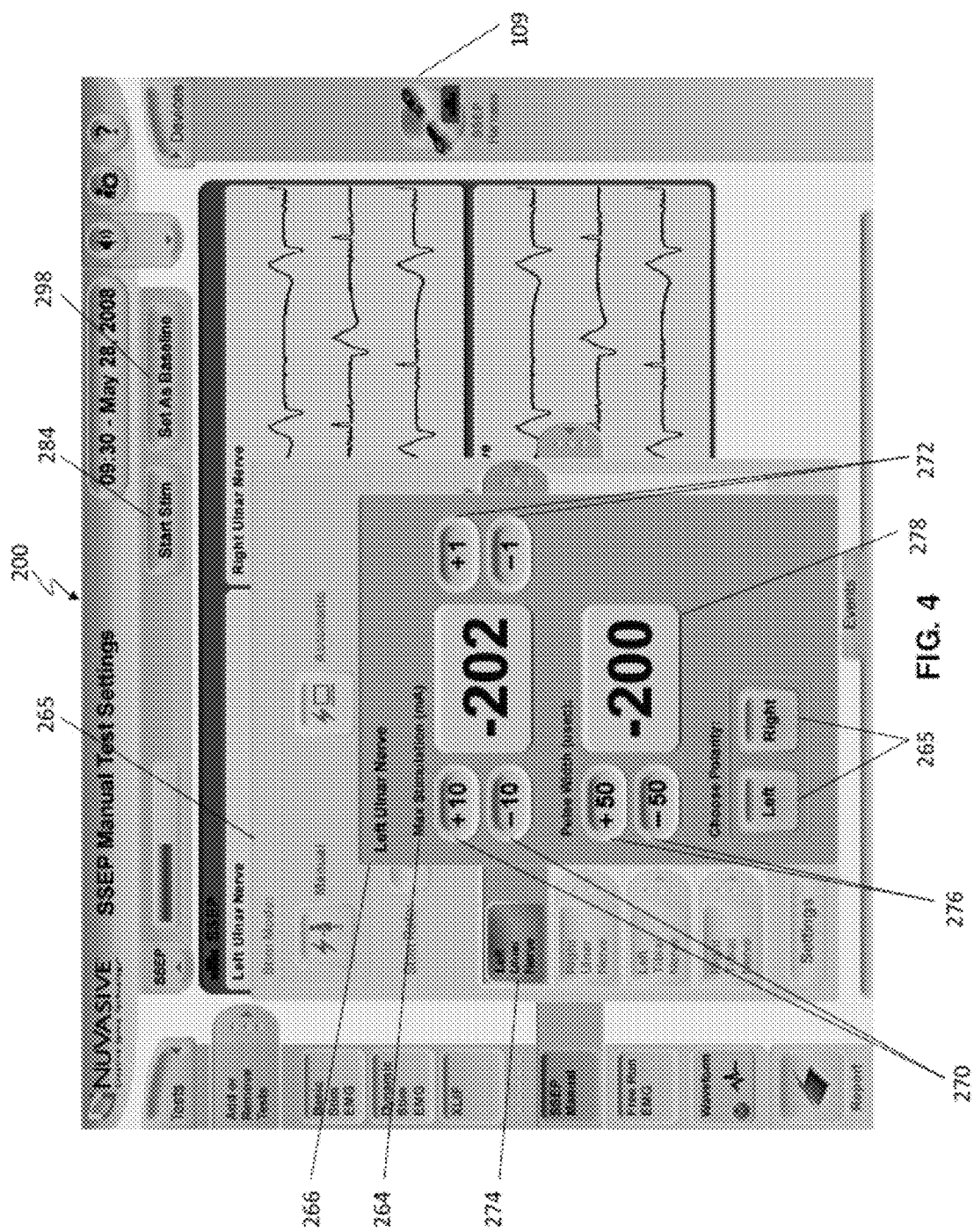
FIG. 4 is an exemplary screen display illustrating a second embodiment of a SSEP Manual Stimulus Mode setting with a Left Ulnar Nerve (LUN) Breakout screen forming part of the neurophysiology system of FIG. 1.

FIGS. 3-8 are exemplary screen displays of the "SSEP Manual" mode according to one embodiment of the neuromonitoring system 10. FIG. 3 illustrates an intra-operative monitoring (TOM) setup screen from which various features and parameters of the SSEP Manual mode may be controlled and/or adjusted by the user as desired. Using this screen, the user has the opportunity to toggle between Manual mode and Automatic mode, select a stimulation rate, and change one or more stimulation settings (e.g. stimulation current, pulse width, and polarity) for each stimulation target site (e.g. left ulnar nerve, right ulnar nerve, left tibial nerve, and right tibial nerve). By way of example only, the user may change one or more stimulation settings of each peripheral nerve by first selecting one of the stimulation site tabs 264.

Figure 18:
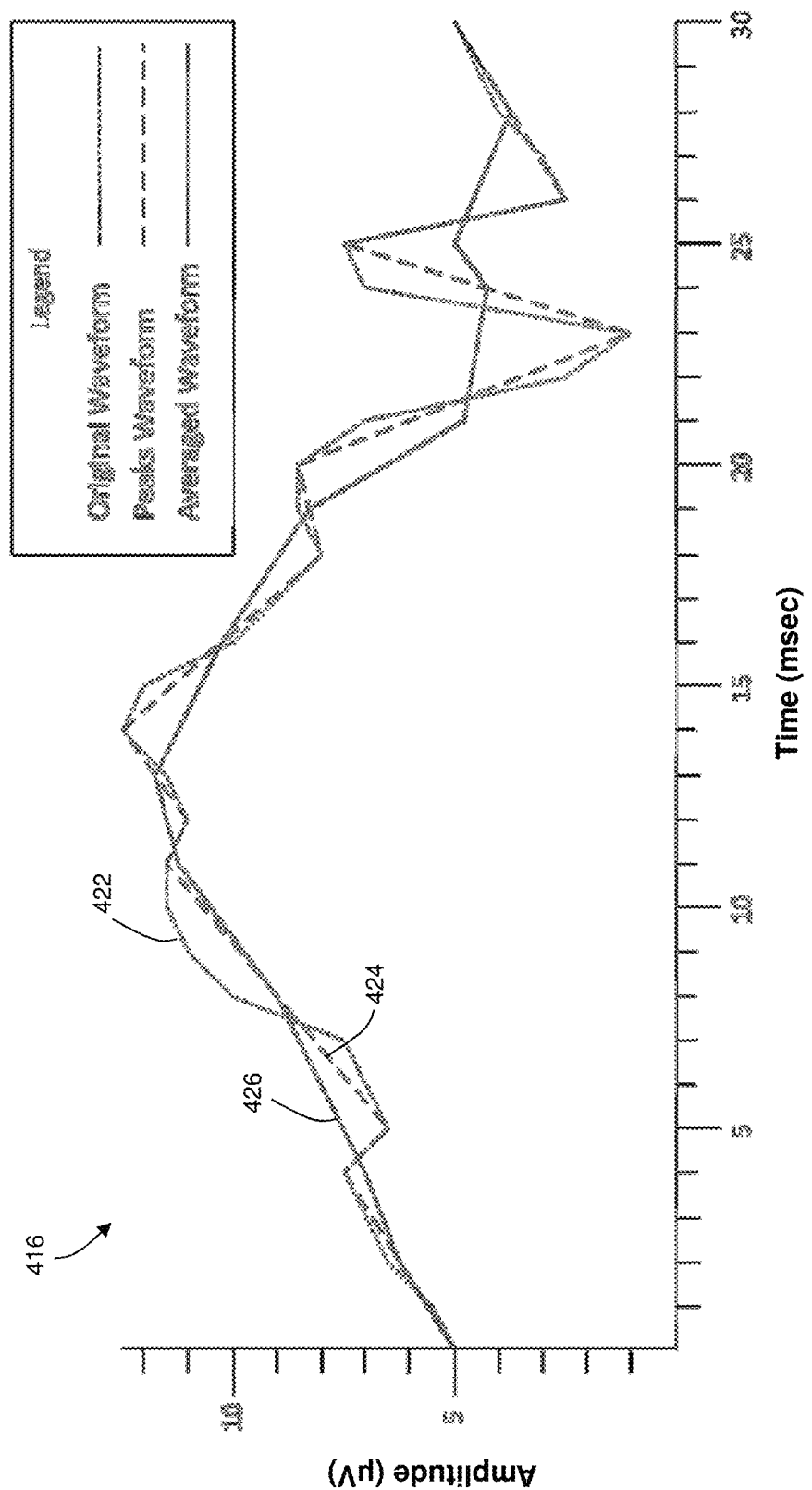
FIG. 18 depicts the resultant waveform after further processing via a third step of the flow chart of FIG. 14.

Selecting one of the stimulation site tabs 264 will open a control window 265, seen in FIG. 18, from which various parameters of the SSPE manual test may be adjusted according to user preference. By way of example only, FIG. 18 is an illustration of an onscreen display for the SSEP manual test settings of the left ulnar nerve stimulation site. The highlighted "Left Ulnar Nerve" stimulation site tab 264 and the pop-up window title 266 indicate that adjusting any of the settings will alter the stimulation signal delivered to the left ulnar nerve. Multiple adjustment buttons are used to set the parameters of the stimulation signal. According to one example, the stimulation rate may be selected from a range between 2.2 and 6.2 Hz, with a default value of 4.7 Hz. The amplitude setting may be increased or decreased in increments of 10 mA using the amplitude selection buttons 270 labeled (by way of example only) "+10" and "−10". More precise amplitude selections may be made by increasing or decreasing the amplitude in increments of 1 mA using the amplitude selection buttons 272 labeled (by way of example only) "+1" and "−1". According to one example, the amplitude may be selected from a range of 1 to 100 mA with a default value of 10 mA. The selected amplitude setting is displayed in box 274. The pulse width setting may be increased or decreased in increments of 50 μsec using the width selection buttons 276 labeled "+50" and "−50". According to one example, the pulse width may be selected from a range of 50 to 300 μsec, with a default value of 200 μsec. The precise pulse width setting 278 is indicated in box 278. Polarity controls 280 may be used to set the desired polarity of the stimulation signal. SSEP stimulation may be initiated at the selected stimulation settings by pressing the SSEP stimulation start button 284 labeled (by way of example only) "Start Stim." Although stimulation settings adjustments are discussed with respect to the left ulnar nerve, it will be appreciated that stimulation adjustments may be applied to the other stimulation sites, including but not limited to the right ulnar nerve, and left and right tibial nerve. Alternatively, as described below, the system 10 may utilize an automated selection process to quickly determine the optimal stimulation parameters for each stimulation channel.

In order to monitor the health of the spinal cord with SSEP, the user must be able to determine if the responses to the stimulation signal are changing. To monitor for this change a baseline is determined, preferably during set-up. This can be accomplished simply by selecting the "set as baseline" button 298 next to the "start stim" button 284 on the setting screen illustrated in FIG. 4. Having determined a baseline recording for each stimulation site, subsequent monitoring may be performed as desired throughout the procedure and recovery period to obtain updated amplitude and latency measurements.

Figure 5:
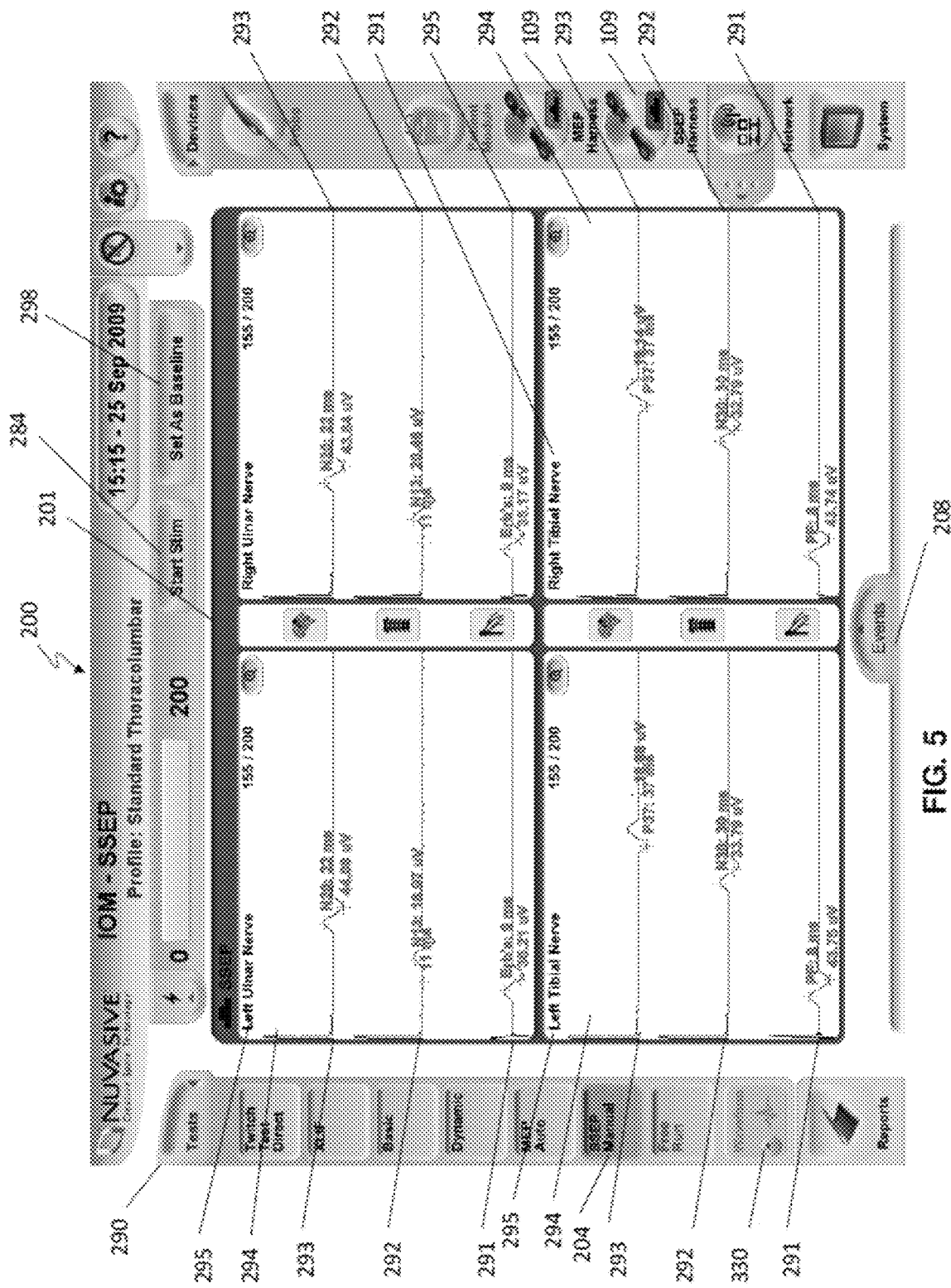
FIG. 5 is an exemplary screen display illustrating one embodiment of an SSEP Manual Run screen forming part of the neurophysiology system of FIG. 1.
Figure 6:
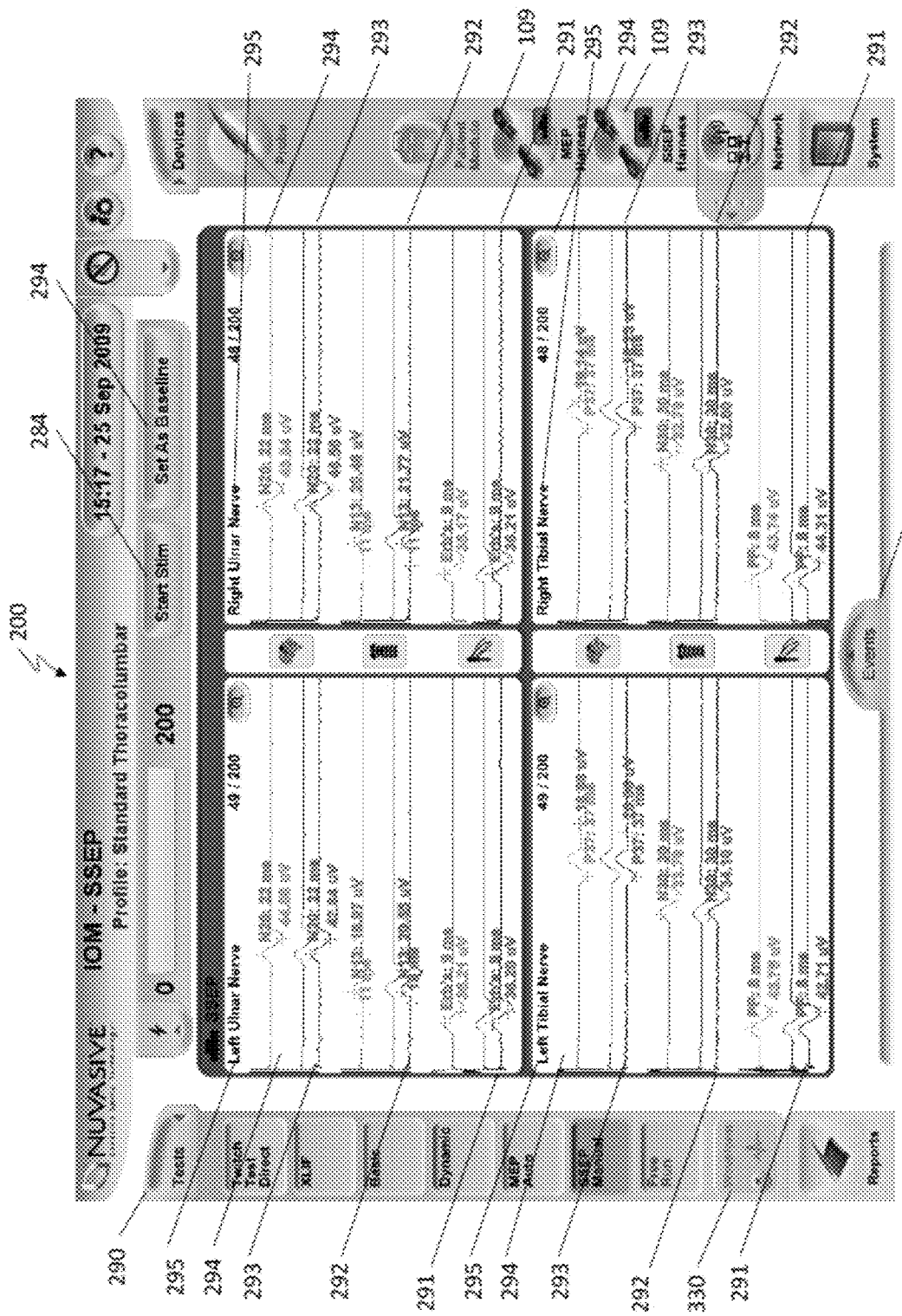
FIG. 6 is an exemplary screen display illustrating a second embodiment of an SSEP Manual Run screen forming part of the neurophysiology system of FIG. 1.
Figure 7:
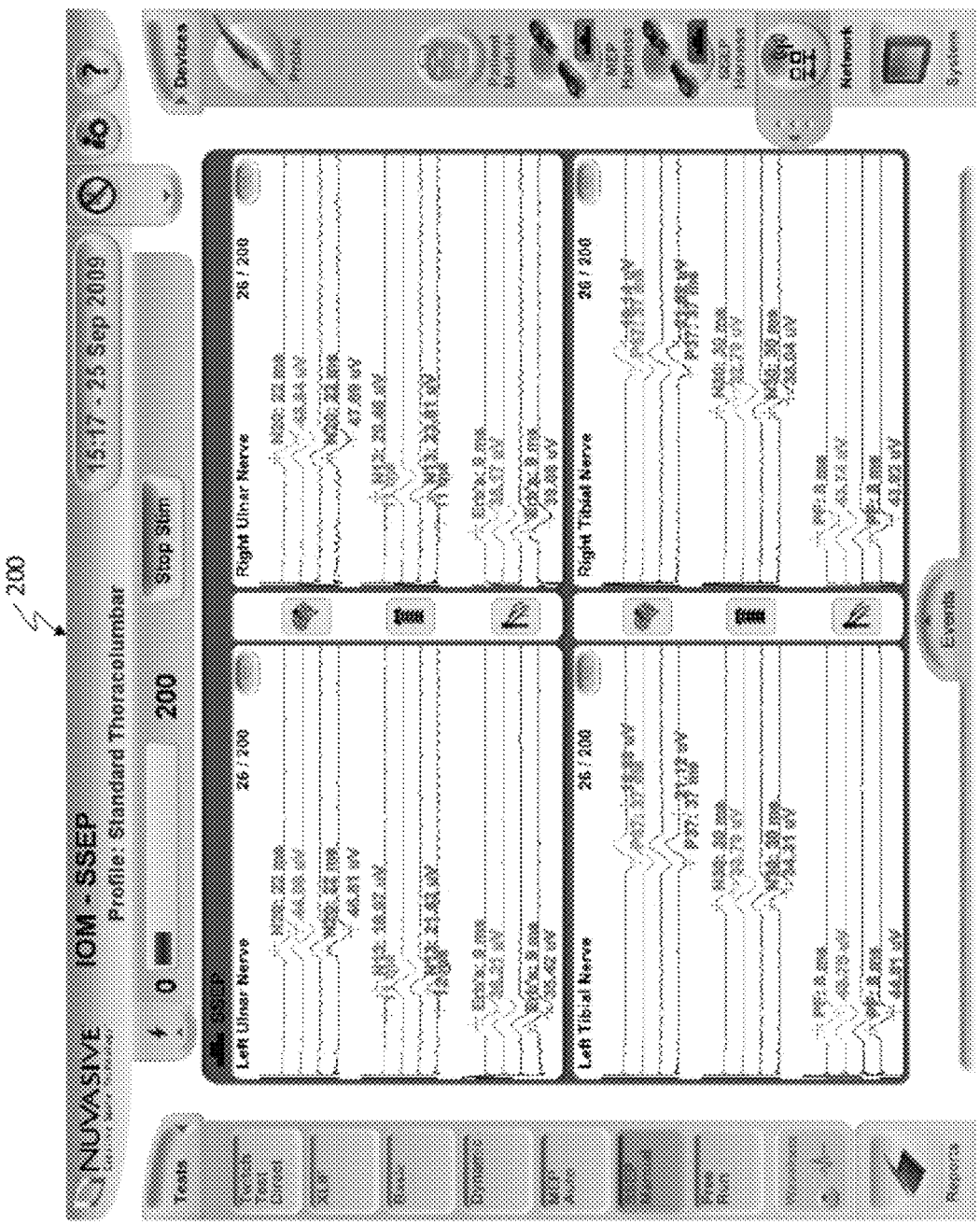
FIG. 7 is an exemplary screen display illustrating a third embodiment of an SSEP Manual Run screen forming part of the neurophysiology system of FIG. 1.
Figure 8:
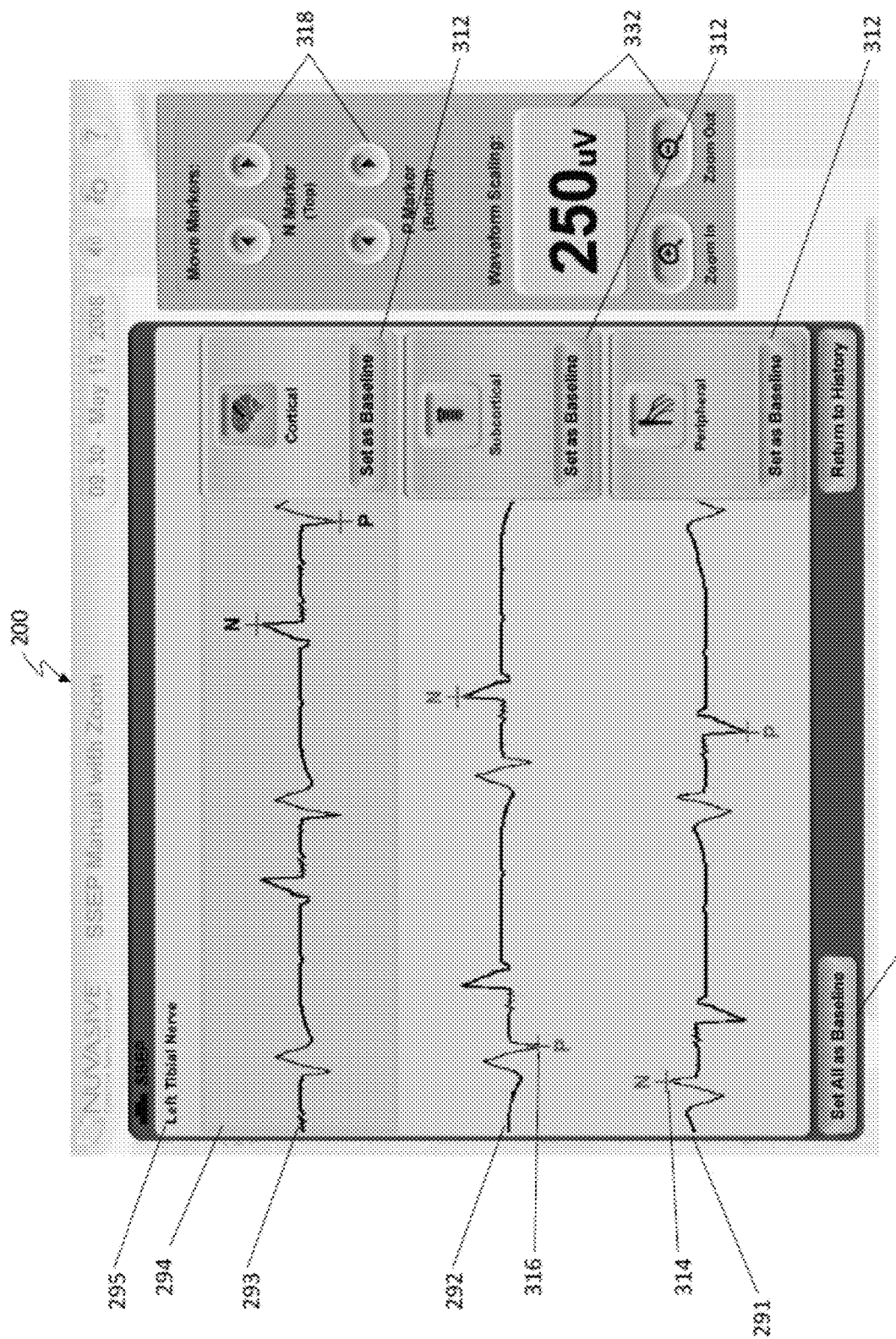
FIG. 8 is an exemplary screen display illustrating a fourth embodiment of an SSEP Manual Run screen forming part of the neurophysiology system of FIG. 1.

FIG. 5 depicts an exemplary screen display for Manual mode of the SSEP monitoring function. A mode indicator tab 290 on the test menu 204 indicates that "SSEP Manual" is the selected mode. The center result area 201 is divided into four sub areas or channel windows 294, each one dedicated to displaying the signal response waveforms for one of the stimulation nerve sites. The channel windows 294 depict information including the nerve stimulation site 295, and waveform waterfalls for each of the recording locations 291-293. For each stimulated nerve site, the system 10 displays three signal response waveforms, representing the measurements made at three different recording sites. By way of example only, the three recording sites are a peripheral 291 (from a peripheral nerve proximal to the stimulation nerve), subcortical 292 (spine), and cortical 293 (scalp), as indicated for example in Table 5 above. Each section may be associated with a pictorial icon, illustrating the neural/skeletal structure. Although SSEP stimulation and recording is discussed with respect to the nerve stimulation site and the recording sites discussed above, it will be appreciated that SSEP stimulation may be applied to any number of peripheral sensory nerves and the recording sites may be located anywhere along the nervous system superior to the spinal level at risk during the procedure.

During SSEP modes (auto and manual), a single waveform response is generated for each stimulation signal run (for each stimulation channel). The waveforms are arranged with stimulation on the extreme left and time increasing to the right. By way of example, the waveforms are captured in a 100 ms window following stimulation. The stimulation signal run is comprised of a predefined number of stimulation pulses firing at the selected stimulation frequency. By way of example only, the stimulation signal may include 300 pulses at a frequency of 4.7 Hz. A 100 ms window of data is acquired on each of three SSEP recording channels: cortical, subcortical, and peripheral. With each successive stimulation on the same channel during a stimulation run, the three acquired waveforms are summed and averaged with the prior waveforms during the same stimulation run for the purpose of filtering out asynchronous events such that only the synchronous evoked response remains after a sufficient number of pulses. Thus, the final waveform displayed by the system 10 represents an averaging of the entire set (e.g. 300) of responses detected.

With each subsequent stimulation run, waveforms are drawn slightly lower each time, as depicted in FIGS. 5-8, until a total of four waveforms are showing. After more than four stimulation runs, the baseline waveform is retained, as well as the waveforms from the previous four stimulation runs. Older waveforms are removed from the waveform display. According to one embodiment, different colors may be used to represent the different waveforms. For example, the baseline waveforms may be colored purple, the last stimulation run may be colored white, the next-to-last stimulation run may be colored medium gray, and the earliest of the remaining stimulation runs may be colored dark gray.

According to one example, the baseline and the latest waveforms may have markers 314, 316 placed indicating latency and amplitude values associated with the waveform. The latency is defined as the time from stimulation to the first (earliest) marker. There is one "N" 314 and one "P" 316 marker for each waveform. The N marker is defined as the maximum average sample value within a window and the P value is defined as the minimum average sample value within the window. The markers may comprise cross consisting of a horizontal and a vertical line in the same color as the waveform. Associated with each marker is a text label 317 indicating the value at the marker. The earlier of the two markers is labeled with the latency (e.g. 22.3 ms). The latter of the two markers is labeled with the amplitude (e.g. 4.2 uV). The amplitude is defined as the difference in microvolts between average sample values at the markers. The latency is defined as the time from stimulation to the first (earliest) marker. Preferably, the markers are placed automatically by the system 10 (in both auto an manual modes). In manual mode, the user may select to place (and or move) markers manually.

Figure 22:
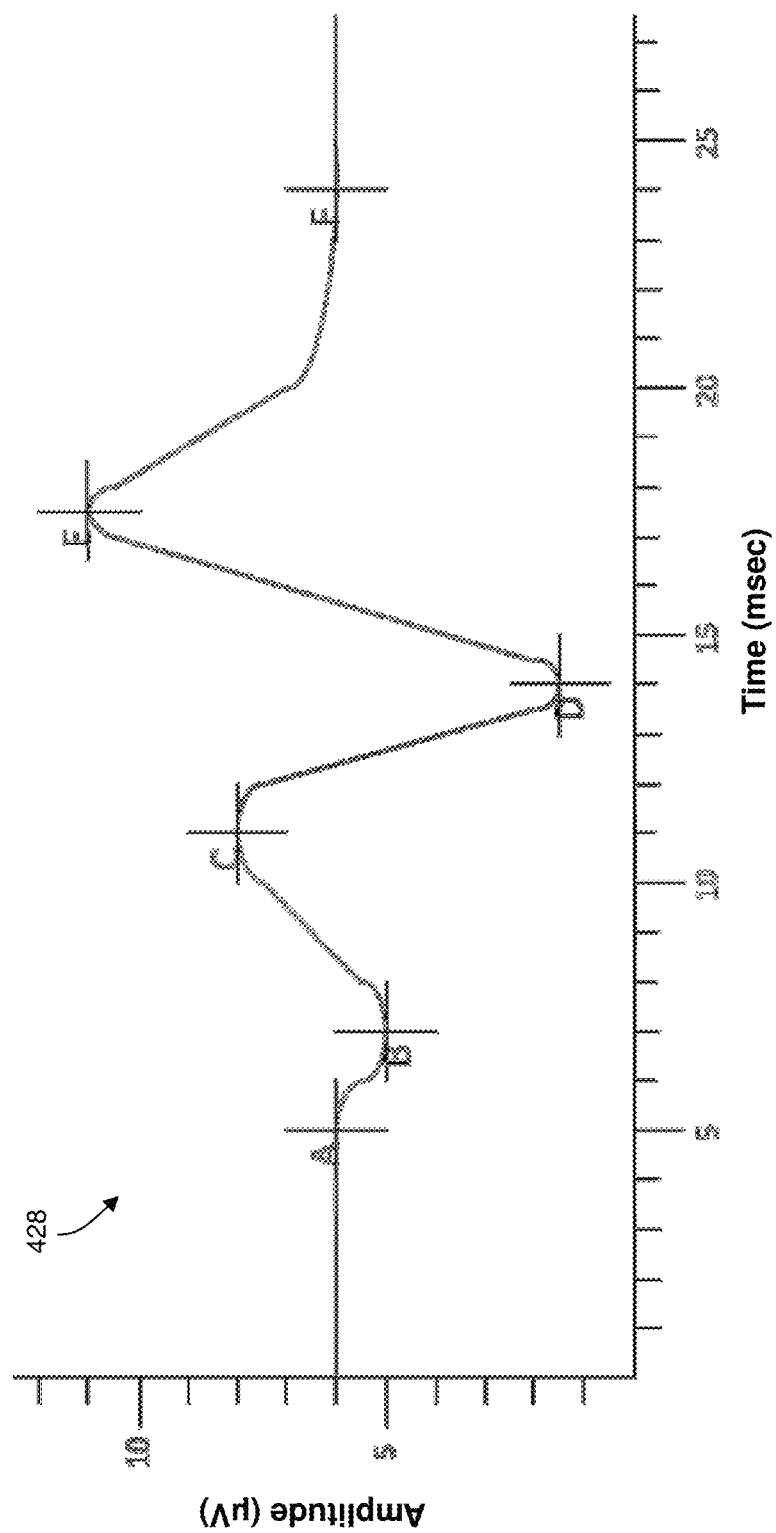
FIG. 22 depicts an example of a first signal classification parameter of the flow chart of FIG. 21.

Further selecting one of the channel windows 294 will zoom in on the waveforms contained in that window 294. FIG. 22 is an example illustration of the zoom view achieved by selecting one of the channel windows 294. The zoom view includes waveforms 291-293, the baseline waveform, markers 314 and 316, and controls for moving markers 318 and waveform scaling 332. Only the latest waveform is shown. The "Set All as Baseline" button 310 will allow the user to set (or change) all three recorded waveforms as the baselines. Additionally, baselines may be set (or changed) individually by pressing the individual "Set as Baseline" buttons 312. Furthermore, the user may also move the N marker 314 and P markers 316 to establish new measurement points if desired. Direction control arrows 318 may be selected to move the N and P markers to the desired new locations. Alternatively, the user may touch and drag the marker 314, 316 to the new location. Utilizing the waveform controls 332 the user may zoom in and out on the recorded waveform.

Figure 9:
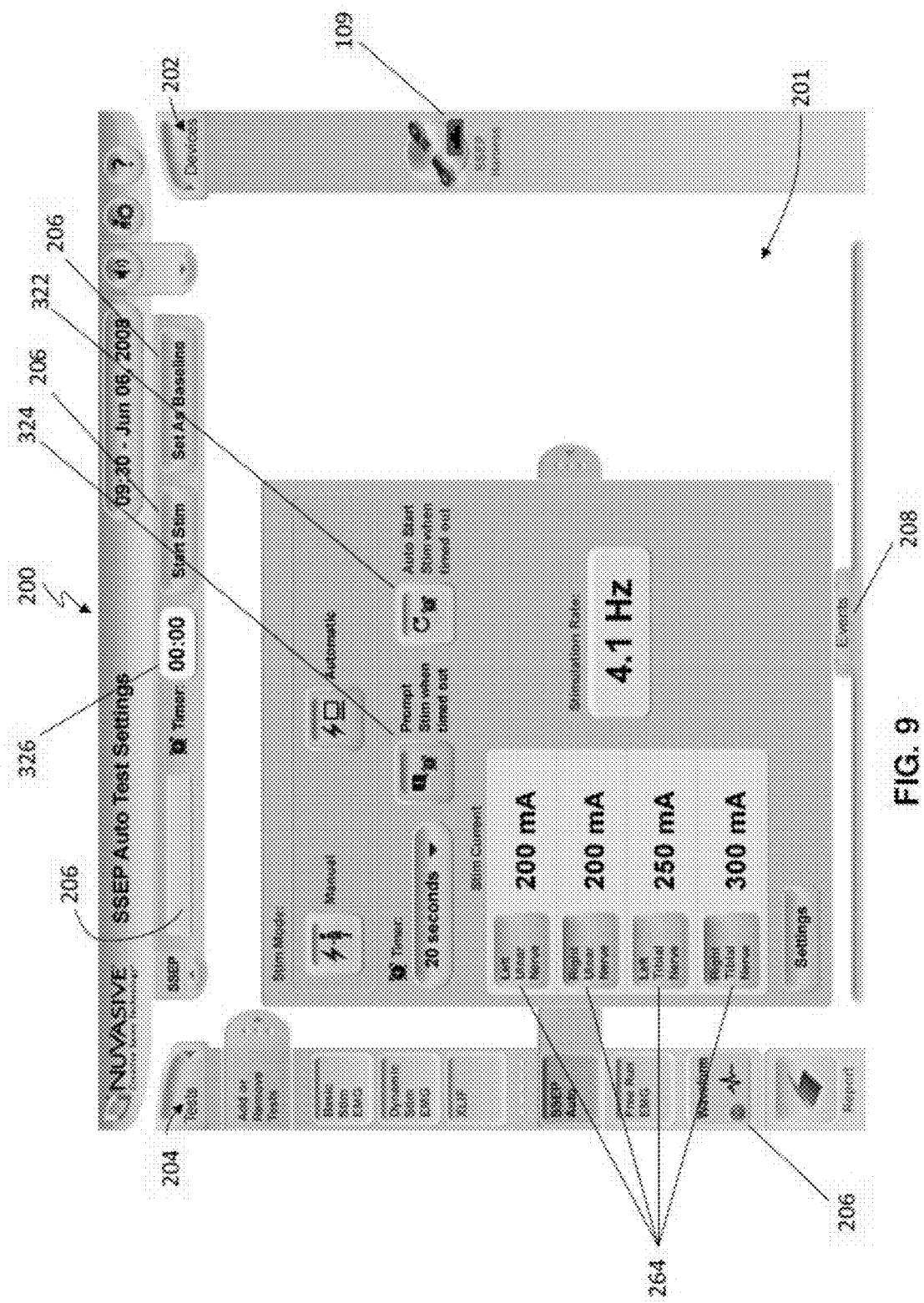
FIG. 9 is an exemplary screen display illustrating one embodiment of an SSEP Automatic Test Setting screen forming part of the neurophysiology system of FIG. 1.

Referencing FIGS. 9-12, Automatic SSEP mode functions similar to Manual SSEP mode except that the system 10 determines the amplitude and latency values and alerts the user if the values deviate. FIG. 9 shows, by way of example only, an exemplary setup screen for the SSEP Automatic mode. In similar fashion to the setup screen previously described for the SSEP Manual mode, the user may toggle between Manual mode and Automatic mode, select a stimulation rate, and change one or more stimulation settings. By way of example only, the user may change one or more stimulation settings of each peripheral nerve by first selecting one of the stimulation site tabs 264, as described above with reference to Manual mode and FIG. 4. According to one example, the stimulation rate may be selected from a range between 2.2 and 6.2 Hz, with a default value of 4.7 Hz, the amplitude may be selected from a range of 1 to 100 mA, with a default value of 10 mA, the pulse width may be selected from a range of 50 to 300 μsec, with a default value of 200 μsec.

In Automatic mode, the surgical system 10 also includes a timer function which can be controlled from the setup screen. Using the timer drop down menu 326, the user may set and/or change a time interval for the timer application. There are two separate options of the timer function: (1) an automatic stimulation on time out which can be selected by pressing the auto start button 322 labeled (by way of example only) "Auto Start Stim when timed out"; and (2) a prompted stimulation reminder on time out which can be selected by pressing the prompt stimulation button 324 labeled (by way of example only) "Prompt Stim when timed out". After each SSEP monitoring episode, the system 10 will initiate a timer corresponding to the selected time interval and, when the time has elapsed, the system will either automatically perform the SSEP stimulation or a stimulation reminder will be activated, depending on the selected option. The stimulation reminder may include, by way of example only, any one of, or combination of, an audible tone, voice recording, screen flash, pop up window, scrolling message, or any other such alert to remind the user to test SSEP again. It is also contemplated that the timer function described may be implemented in SSEP Manual mode.

Figure 10:
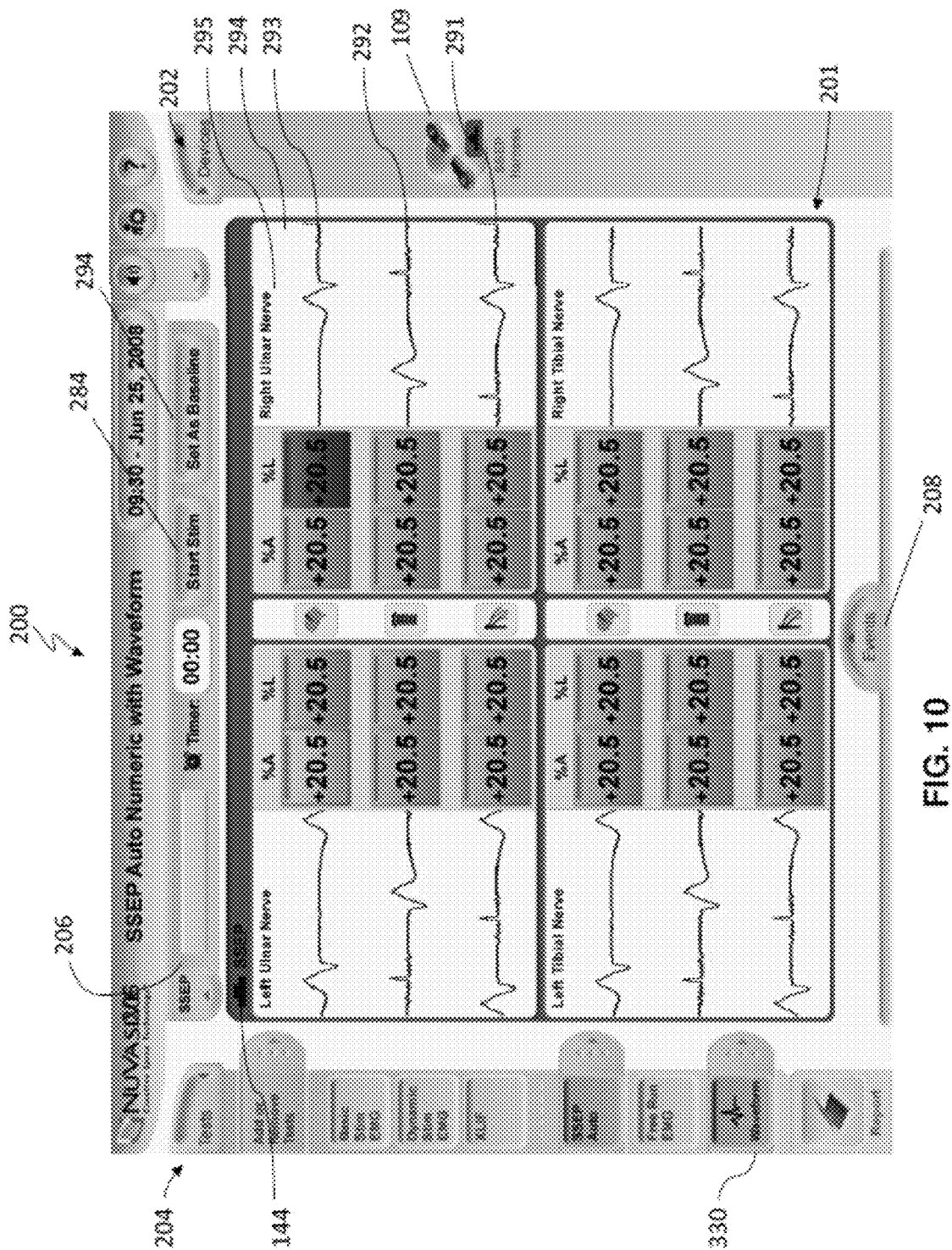
FIG. 10 is an exemplary screen display illustrating one embodiment of an SSEP Automatic Run screen forming part of the neurophysiology system of FIG. 1.
Figure 11:
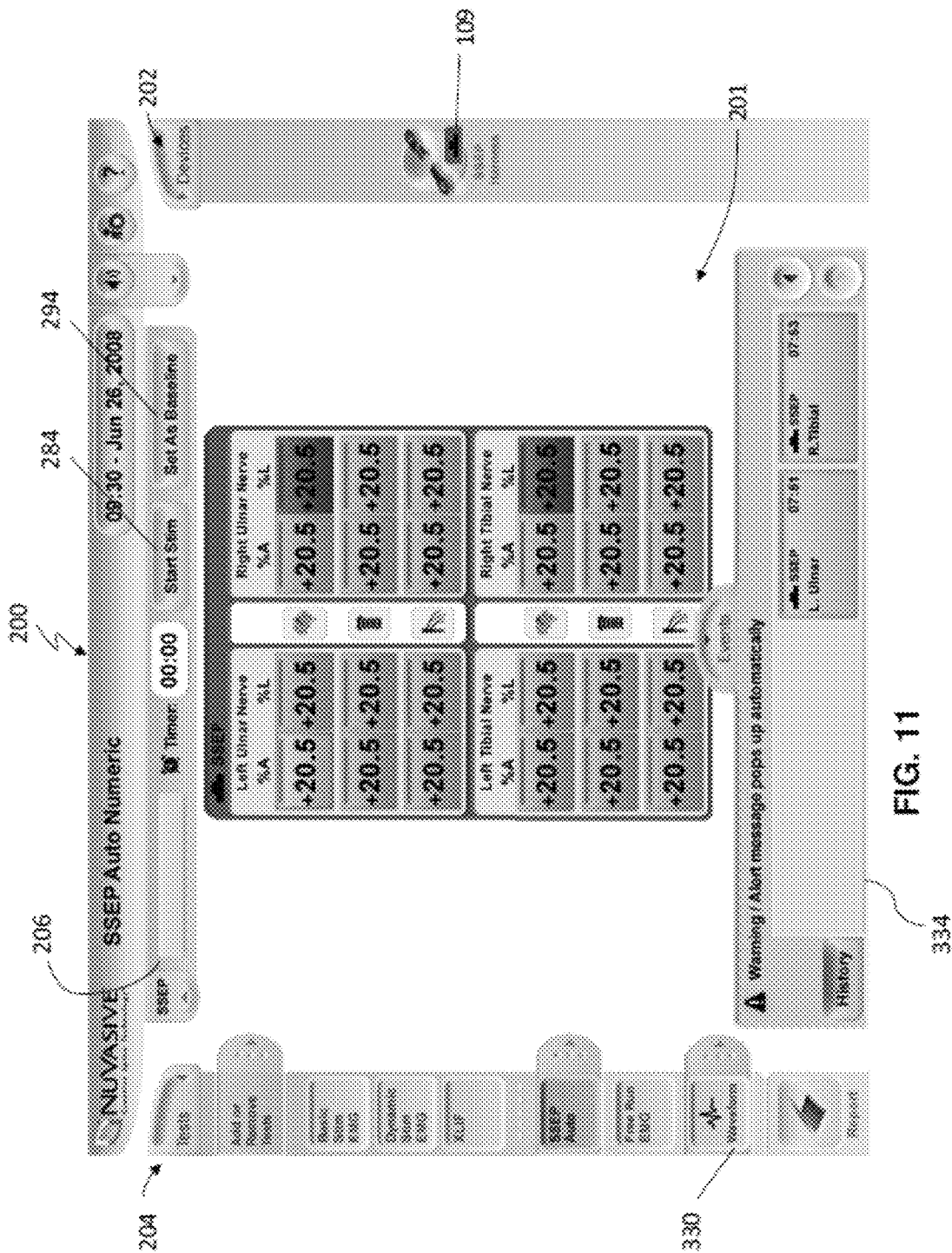
FIG. 11 is an exemplary screen display illustrating a second embodiment of an SSEP Automatic Run screen forming part of the neurophysiology system of FIG. 1.
Figure 12:
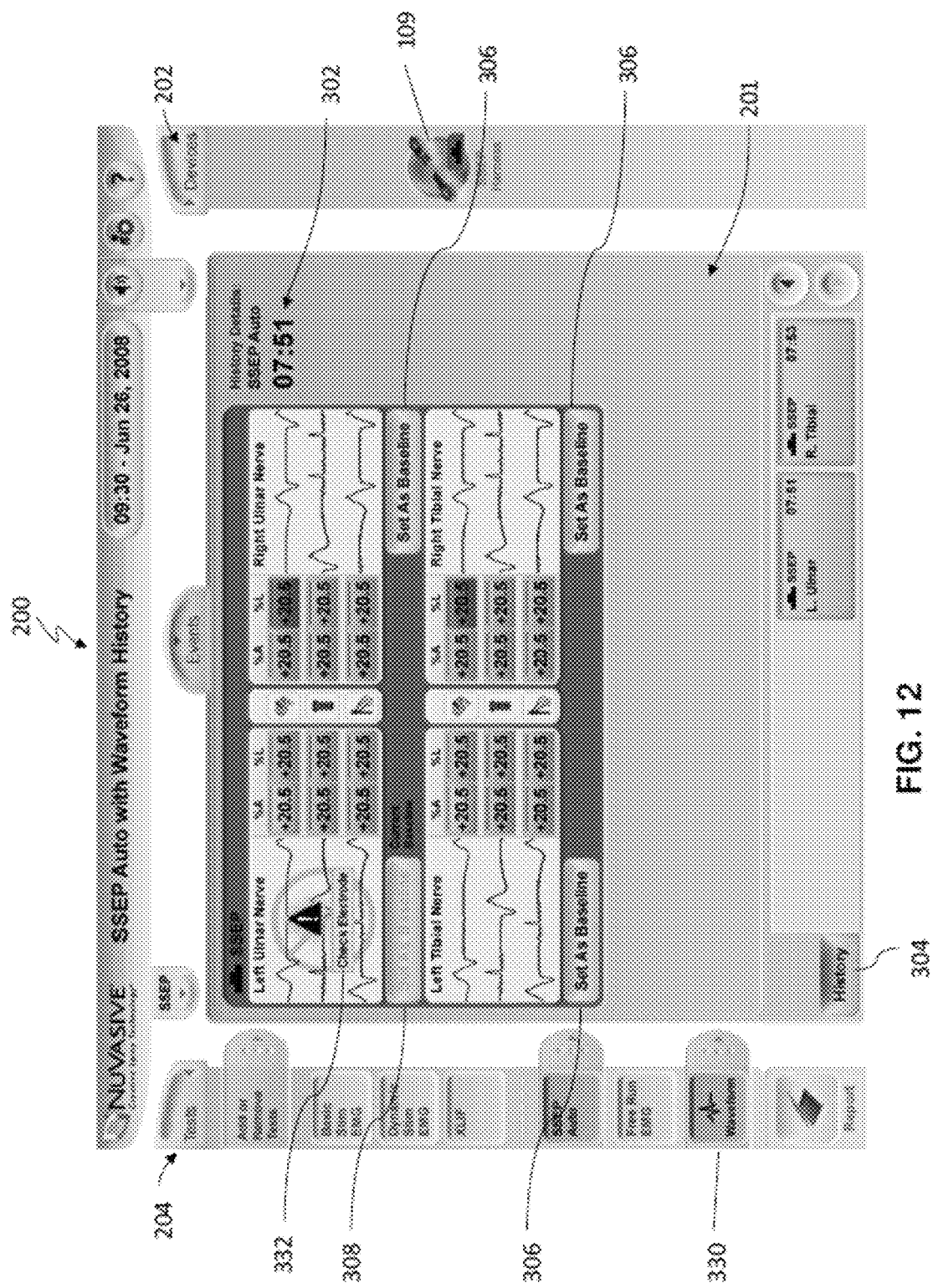
FIG. 12 is an exemplary screen display illustrating a third embodiment of an SSEP Automatic Run screen forming part of the neurophysiology system of FIG. 1.
Figure 24:
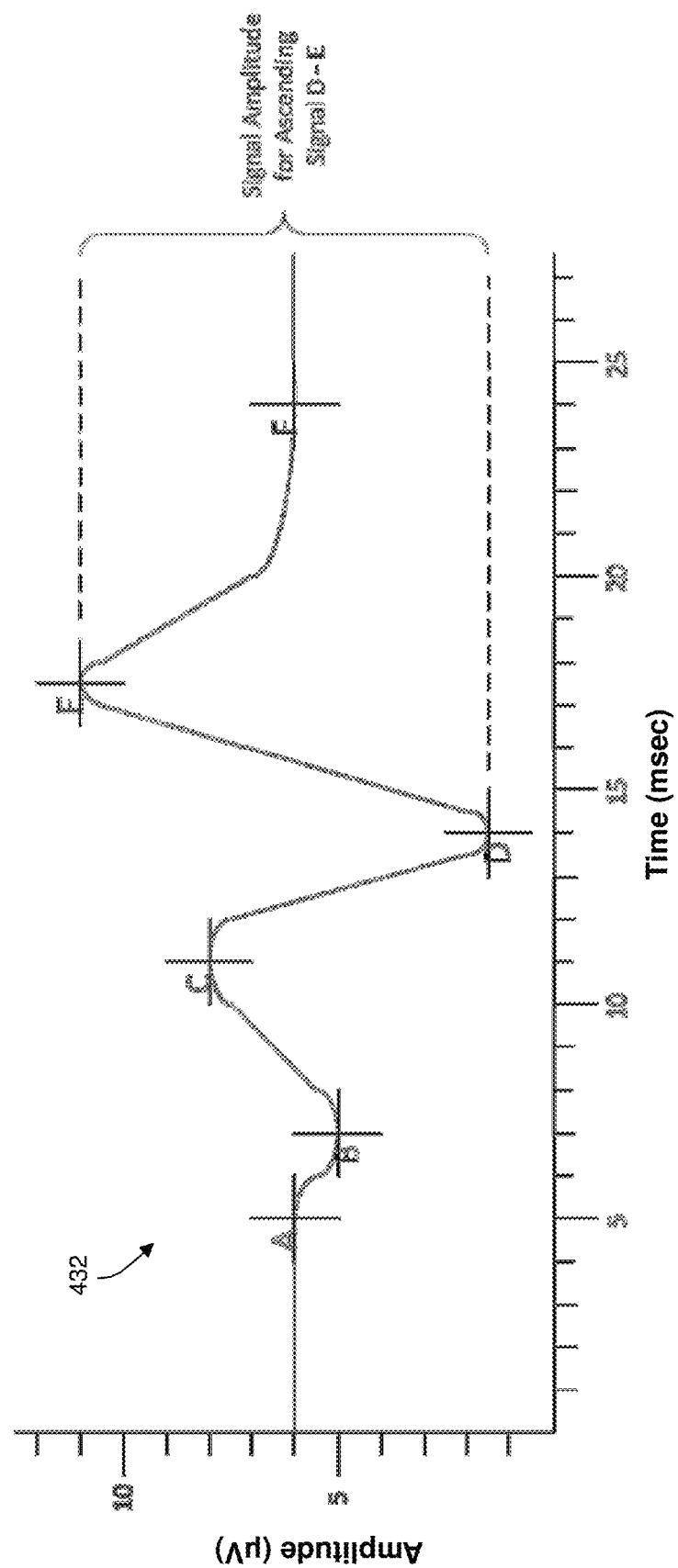
FIG. 24 depicts an example of a third signal classification parameter of the flow chart of FIG. 21.

FIGS. 10-12 depict exemplary onscreen displays for Automatic mode of the SSEP function. According to one embodiment, the user may select to view a screen with only alpha-numeric information (FIG. 25) and one with alpha-numeric information and recorded waveforms (FIG. 24). A mode indicator tab 290 indicates that "SSEP Auto" is the selected mode. A waveform selection tab 330 allows the user to select whether waveforms will be displayed with the alpha-numeric results. In similar fashion to the onscreen displays previously described for the SSEP Manual mode, the system 10 includes a channel window 294 for each nerve stimulation site. The channel window 294 may display information including the nerve stimulation site 295, waveform recordings, and associated recording locations 291-293 (peripheral, sub cortical, and cortical) and the percentage change between the baseline and amplitude measurements and the baseline and latency measurements. By way of example only, each channel window 294 may optionally also show the baseline waveform and latest waveform for each recording site. In the event the system 10 detects a significant decrease in amplitude or an increase in latency, the associated window may preferably be highlighted with a predetermined color (e.g. red) to indicate the potential danger to the surgeon. Preferably, the stimulation results are displayed to the surgeon along with a color code so that the user may easily comprehend the danger and corrective measures may be taken to avoid or mitigate such danger. This may for example, more readily permit SSEP monitoring results to be interpreted by the surgeon or assistant without requiring dedicated neuromonitoring personnel. By way of example only, red is used when the decrease in amplitude or increase in latency is within a predetermined unsafe level. Green indicates that the measured increase or decrease is within a predetermined safe level. Yellow is used for measurements that are between the predetermined unsafe and safe levels. By way of example only, the system 10 may also notify the user of potential danger through the use of a warning message 334. Although the warning message is in the form of a pop-up window, it will be appreciated that the warning may be communicated to the user by any one of, or combination of, an audible tone, voice recording, screen flash, scrolling message, or any other such alert to notify the user of potential danger With reference to FIG. 12 at any time during the procedure, a prior stimulation run may be selected for review. This may be accomplished by, for example, by opening the event bar 208 and selecting the desired event. Details from the event are shown with the historical details denoted on the right side of the menu screen 302 and waveforms shown in the center result screen. Again, the user may chose to reset baselines for one or more nerve stimulation sites by pressing the appropriate "Set As Baseline" button 306. In the example shown, the system 10 illustrates the waveform history at the 07:51 minute mark which is denoted on the right side of the menu screen 302. Prior waveform histories are saved by the surgical system 10 and stored in the waveform history toolbar 304. The describe only in relation to the SSEP Auto function it will be appreciated that the same features may be accessed from SSEP Manual mode, the user may choose to set a recorded stimulation measurement as the baseline for each nerve stimulation site by pressing the "Set As Baseline" button 306. By way of example only, the system 10 will inform the user if the applicable event is already the current baseline with a "Current Baseline" notification 308.

Figure 13:
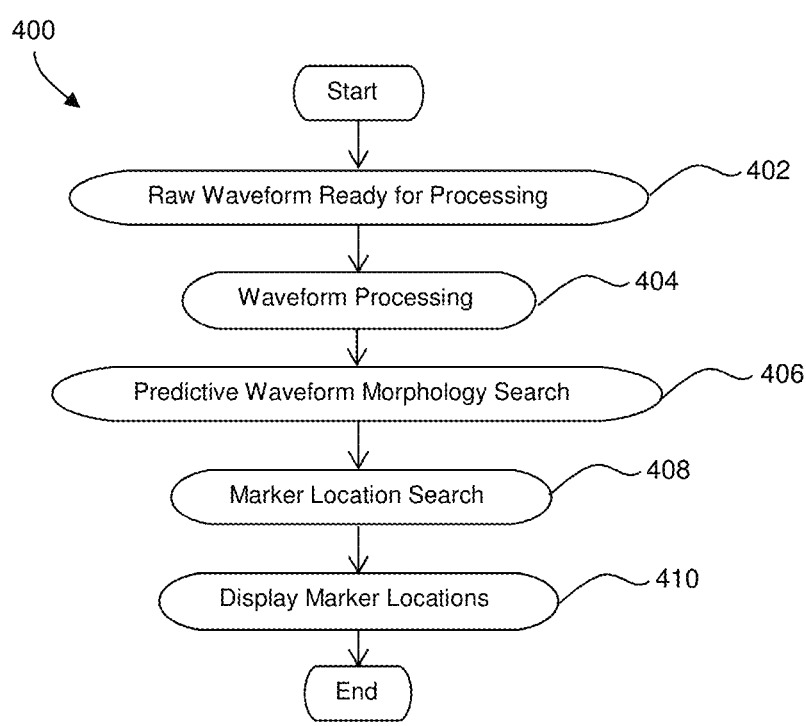
FIG. 13 is a flow chart detailing the steps of the waveform marker placement algorithm according to one embodiment.
Figure 14:
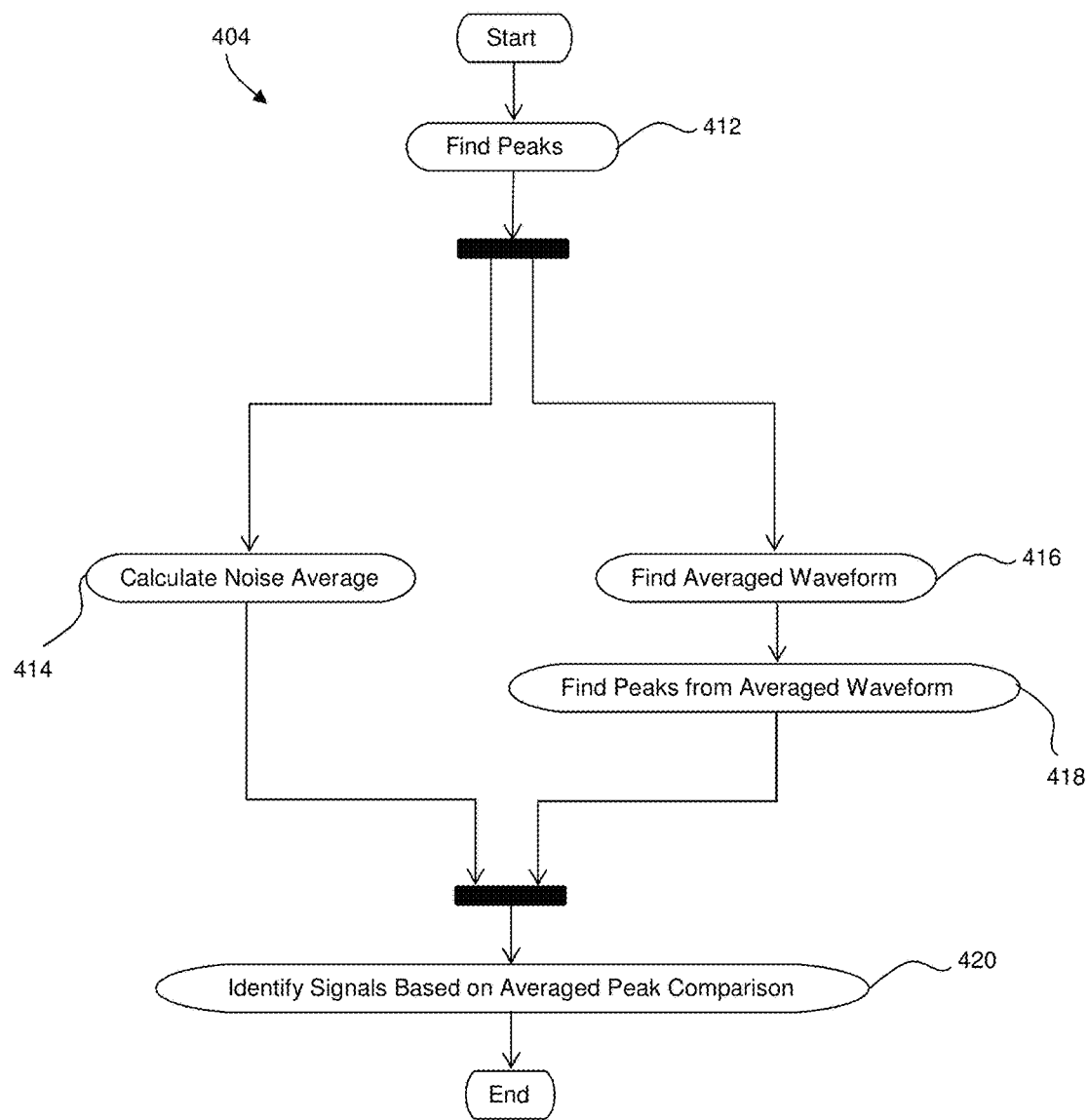
FIG. 14 is a flow chart detailing the steps involved in the waveform processing portion of the algorithm of FIG. 13.

The waveform marker placement algorithm of the present invention will now be described in detail. According to a broad aspect, the waveform marker placement algorithm takes an iterative approach to identifying negative (N) and positive (P) peaks within a waveform and identifying where the N and P latency markers should be placed based on static and dynamic search windows. FIG. 13 is a flowchart of the general steps involved in waveform marker placement in accordance with the algorithm of the present invention. For the purposes of illustration, the algorithm 400 encompasses the waveform data processing and marker search steps for an individual waveform from a single channel. It is contemplated that these steps may be performed on multiple channels either in series or simultaneously. For purposes of illustration, the algorithm is 400 split into three sub-algorithms: a waveform processing algorithm 404, a predictive waveform morphology search algorithm 406; and a waveform marker location algorithm 408 and these sub-algorithms will be designated as such throughout this disclosure. As depicted in the flowchart in FIG. 13, at step 402, the algorithm processor receives a raw waveform 422 ready for processing; at step 404, the waveform is processed to determine what can and cannot be a possible neurophysiologic response; at step 406, the a predictive waveform morphology search is performed on the processed waveform to identify signals that match neurophysiologic waveform morphology criteria; at step 408, a marker location search is performed on the waveform processed at step 408 to determine where N and P latency markers should be placed on the neurophysiologic signal, and at step 510, the determined marker placement locations are displayed on the neurophysiologic response waveform on display 34 of control unit 12.

Waveform Processing

Figure 15:
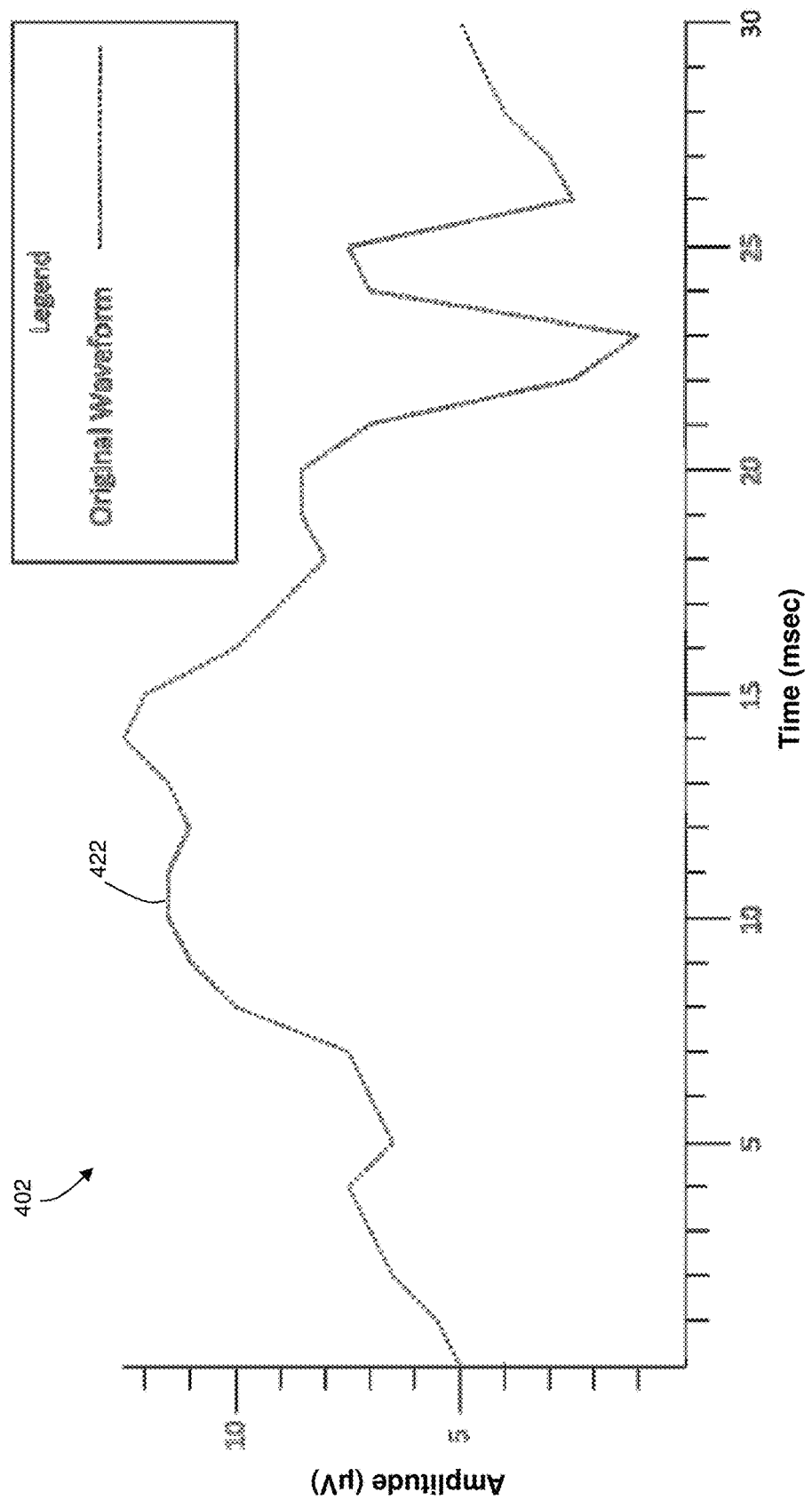
FIG. 15 depicts an example raw waveform to be processed according to the waveform marker placement algorithm of FIG. 13.
Figure 16:
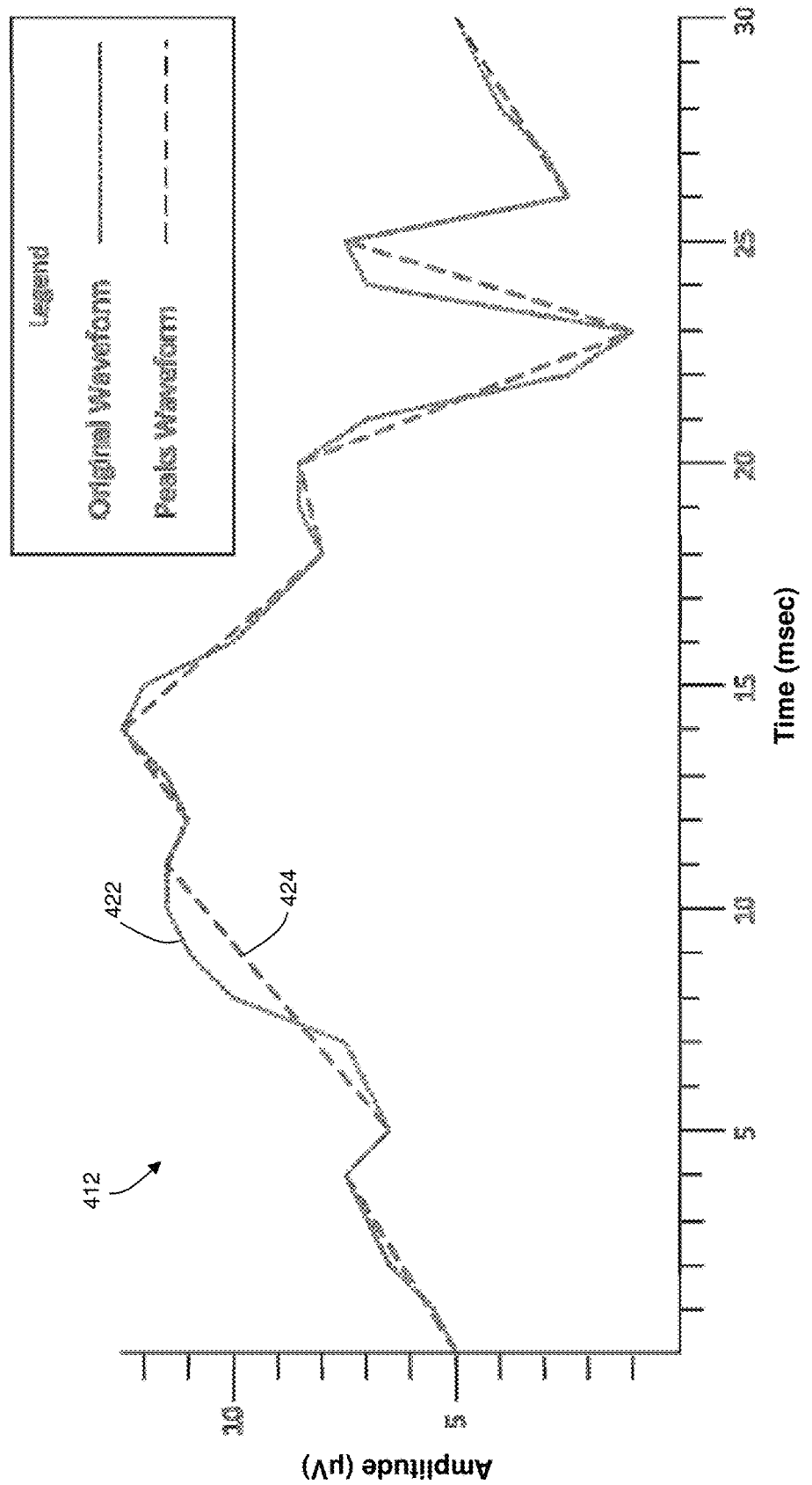
FIG. 16 depicts the resultant waveform after processing via a first step of the flow chart of FIG. 14.

FIGS. 14-20 detail the steps of the waveform processing sub-algorithm 404 in greater detail. For illustrative purposes, the waveform data set of FIG. 15 will be used, where appropriate, to illustrate the successive steps of the algorithm 400 and sub-algorithms 404, 406, 408. At step 402, the raw waveform data 422 is first passed into the algorithm processor. At step 412, the raw waveform data is processed to determine the ascending and descending peaks within the waveform. According to one embodiment, the algorithm finds directional changes in the waveform trend from ascending to descending and descending to ascending. The diagram of FIG. 16 illustrates how the peaks would be determined after the completion of step 412 and how the peaks waveform 424 compares to the original (raw) waveform 422.

The peaks information obtained at step 412 may then be used to identify noise spikes and calculate a noise level for the waveform. According to one embodiment, the noise level may be calculated by finding signal rise transitions that are less than a given sample threshold, adding up their amplitudes and multiplying that result by the time duration of the noise spike, and dividing that number by the total number of samples used in the calculation.

Figure 17:
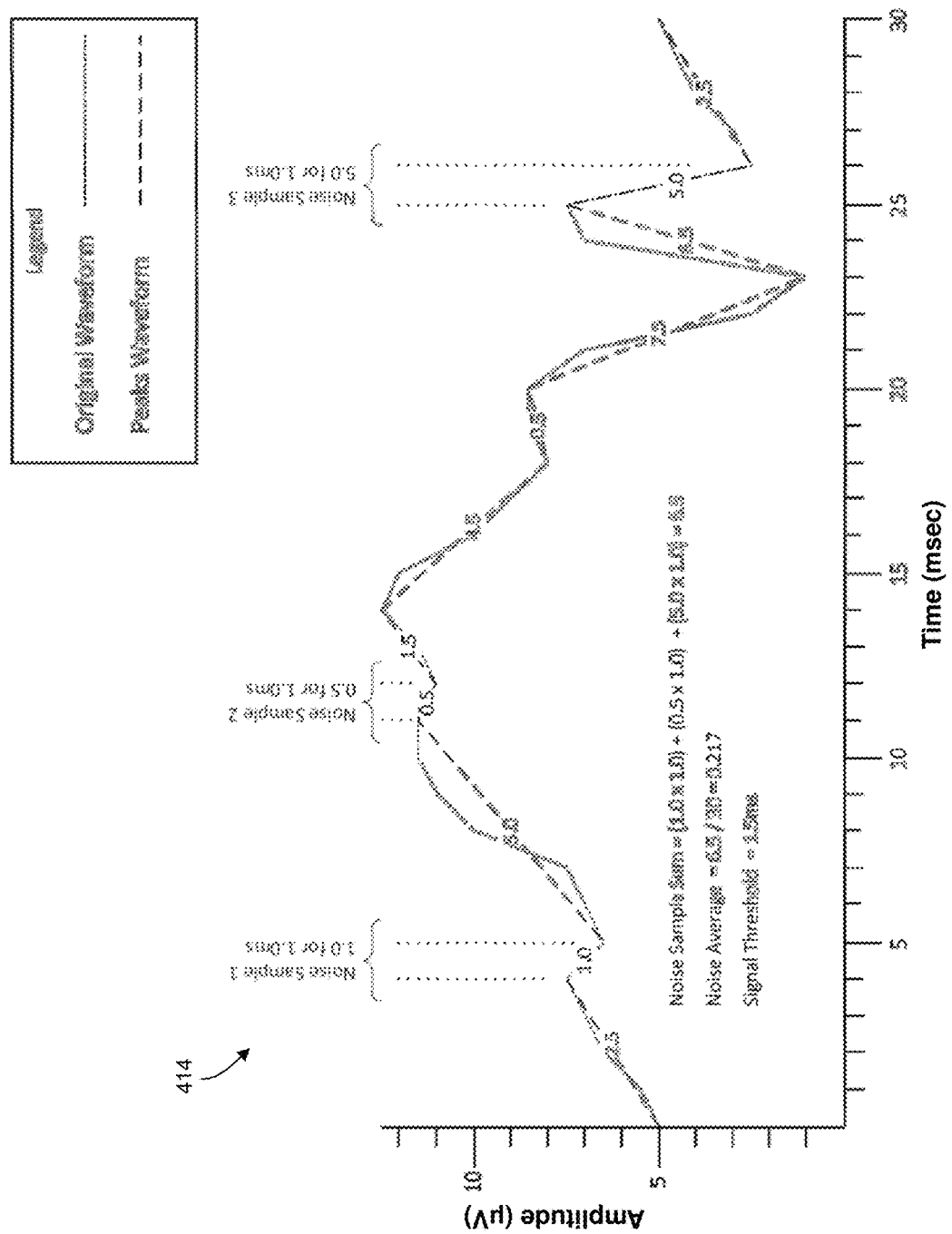
FIG. 17 depicts the resultant waveform after further processing via a second step of the flow chart of FIG. 14.

FIG. 17 depicts step 414 and details how the noise average is calculated on the waveform data set of FIG. 15. For purposes of illustration, a signal threshold of 1.5 msec is selected. As shown in FIG. 17, there are three noise samples that would qualify with a duration of less than 1.5 msec. Noise Sample 1 has an amplitude of 1.0 µV and a duration of 1.0 msec; Noise Sample 2 has an amplitude of 0.5 µV and a duration of 1.0 msec; and Noise sample 3 has an amplitude of 5.0 µV and a duration of 1.0 msec. Multiplying the amplitude of each sample by its respective duration gives a noise sample sum of 6.5. The noise sample is divided by the time base (30 msec) and results in a noise average of 0.217. According to one or more implementations, the algorithm may exclude an early latency portion of the waveform from the noise calculation to disqualify any stimulus artifact present at the onset of the waveform from entering into the noise average calculation.

Figure 19:
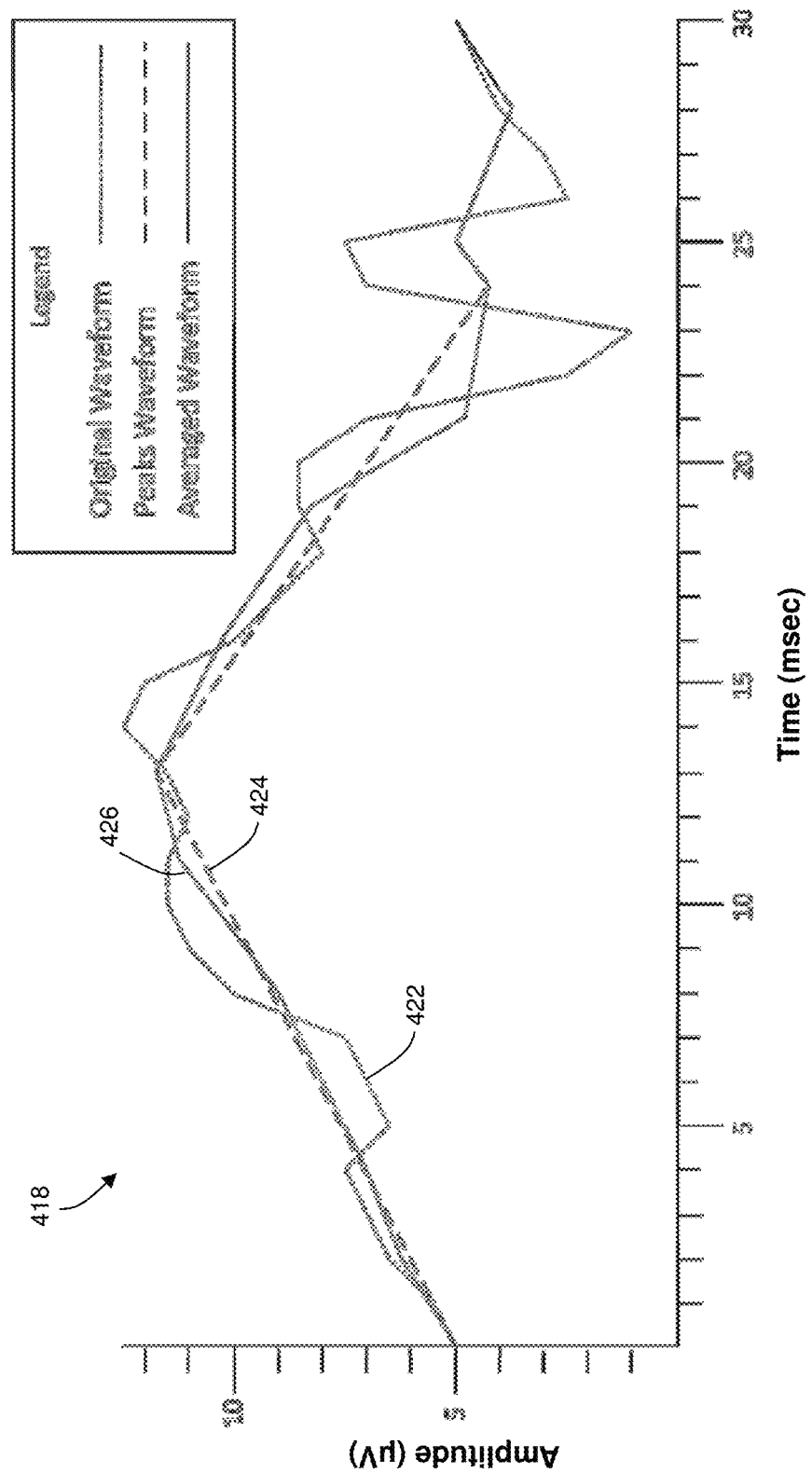
FIG. 19 depicts the resultant waveform after further processing via a fourth step of the flow chart of FIG. 14.

To prevent small noise peaks as being considered as the end of a detected signal (or perhaps the beginning of a new signal), an averaged waveform may be found (step 416). To find the averaged waveform, according to one embodiment, the peaks waveform obtained at step 412 may be used and each of the line segments may be bisected to find the averaged waveform. FIG. 18 shows the averaged waveform 426 as the bisection of the peaks waveform 424. According to one embodiment, when a bisected line value falls in between two waveform indices (amplitude values) the prior lower of the two indices may be used. For illustrative purposes, if a point is to fall between index 4 and 5, the averaged point will be 4. If a point is to fall between index 4 and 6, the index for the averaged point will be 5). Once the small noise peaks are minimized, the averaged waveform 426 may then be processed at step 418 to ascertain its ascending and descending peaks which allows the algorithm to determine where the true peaks are by eliminating possible noise components (FIG. 19).

Figure 20:
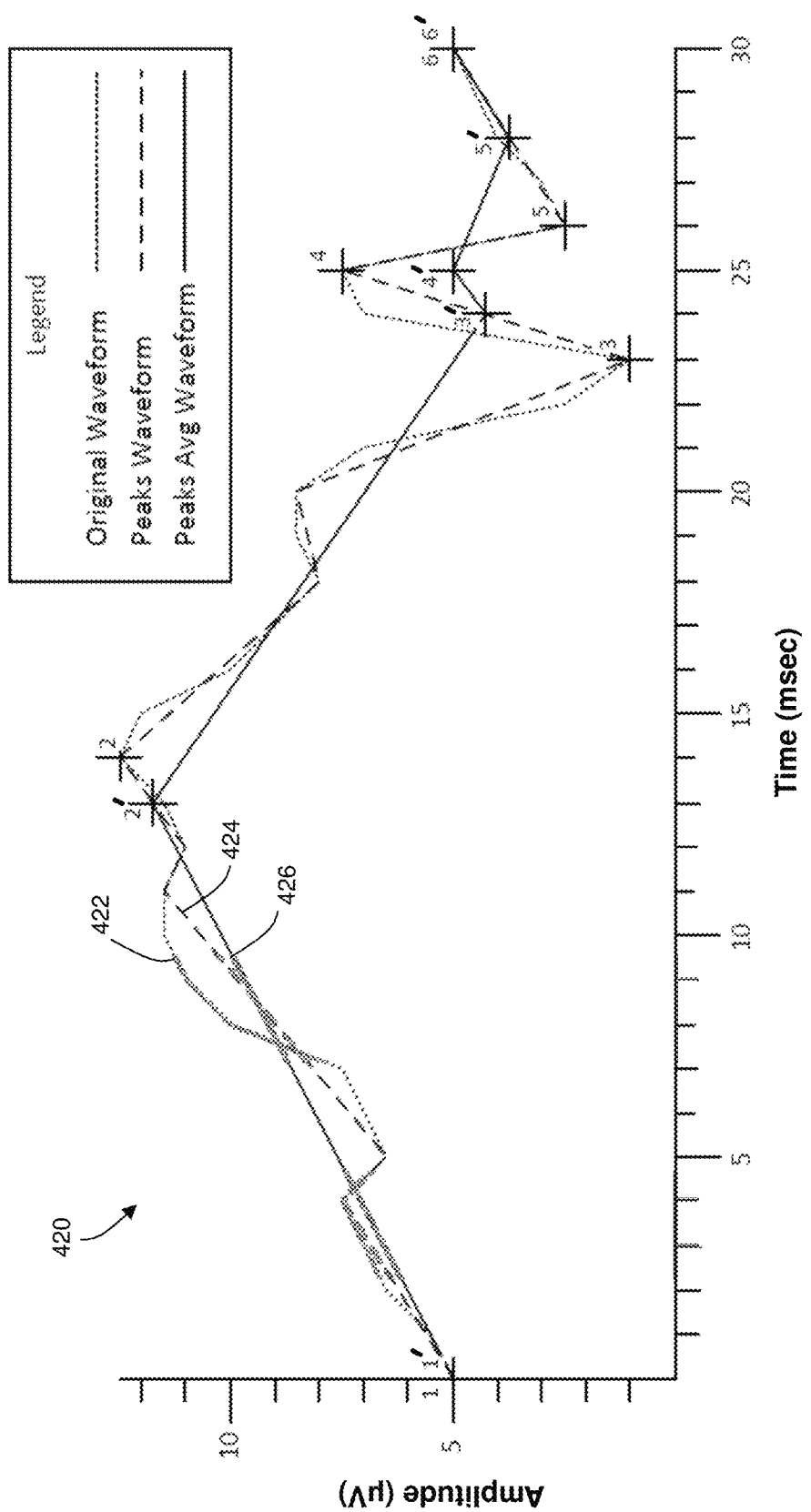
FIG. 20 depicts the resultant waveform after further processing via a fifth step of the flow chart of FIG. 14.

At step 420, the signals are identified based on an averaged peak comparison. As a threshold matter, any potential signal must first meet minimum rise time and minimum signal amplitude values to be qualified as a signal. For example, according to one embodiment, any potential signal of less than 0.5 µV in amplitude and an ascending or descending transition time of less than 0.5 msec may be ignored by the algorithm. As depicted in FIG. 20, the peaks of the averaged waveform 424 are compared against the peaks 422 discovered in the raw waveform to determine where those averaged peaks 424 are located in the original raw waveform 422. It is to be appreciated that it is important to determine where the averaged peaks are in the original waveform since the original waveform is what is plotted for display to the user. For illustrative purposes only, the peaks in the original waveform are designated as numbers 1-6 and the peaks in the averaged waveform are designated as numbers 1'-6'.

Predictive Waveform Morphology Search

Figure 21:
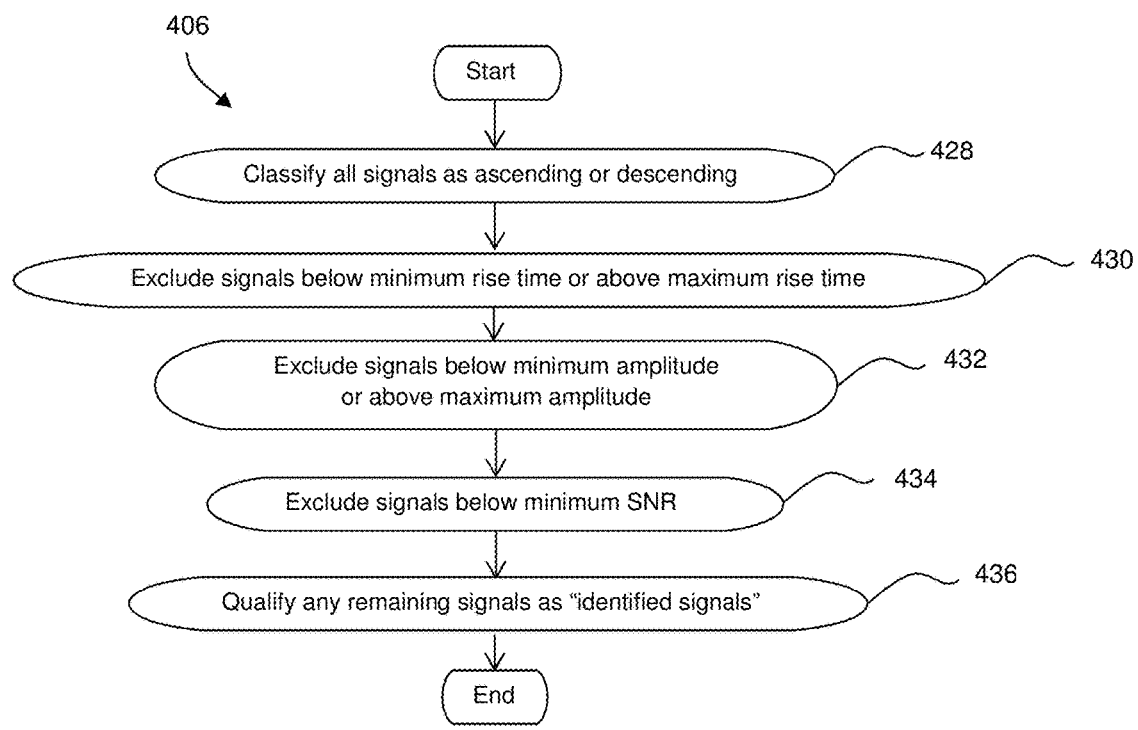
FIG. 21 is a flow chart detailing the steps of the predictive waveform morphology search portion of the algorithm of FIG. 13.

With respect to FIGS. 21-26, the predictive waveform morphology sub-algorithm 406 will now be discussed in greater detail. With the raw waveform processed and signals that cannot be considered as likely neurophysiologic signals excluded, the algorithm proceeds to step 406 and searches each waveform for a particular morphology based on any number of searchable parameters. This particular morphology may include certain characteristics of an SSEP response. By way of example, the searchable parameters may be: signal rise type, minimum and maximum signal rise times, minimum and maximum signal amplitudes, and minimum signal to noise ratio as shown in the flowchart of FIG. 21. Each of these searchable parameters will be discussed in turn below.

The predictive waveform morphology sub-algorithm 406 may classify all signals within a waveform as ascending or descending (step 428). The algorithm 406 can search for either ascending or descending signals when the rise type can be predicted as well as when the rise type cannot be predicted. In the example waveform of FIG. 22, the signals are classified based on rise type according to the results of Table 2:

TABLE 2

| Rise Type | Results |
|---|---|
| Ascending | B&C |
|  | D&E |
| Descending | A&B |
|  | C&D |
|  | E&F |

The predictive waveform morphology sub-algorithm 406 may then classify all signals within a waveform based on the signal rise time (step 430). The signal rise time is the measure of the entire time an ascending or descending signal trends in that direction. The minimum signal rise time defines the minimum time this trend must take before it is considered a valid neurophysiologic signal. The maximum signal rise time defines the maximum time this trend may take before it is considered an invalid signal. These considerations may help discount noise spikes from being classified as valid signals.

Figure 23:
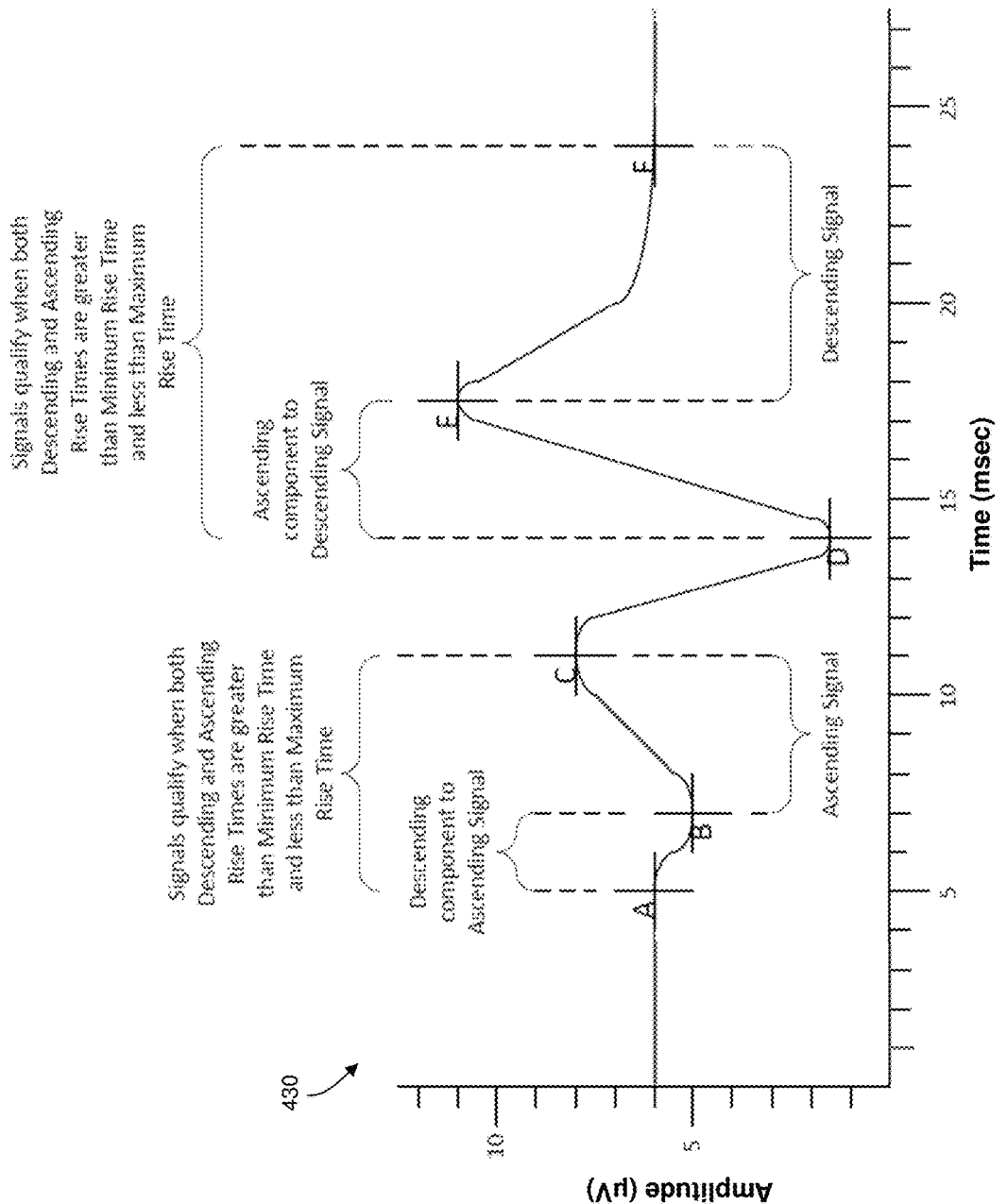
FIG. 23 depicts an example of a second signal classification parameter of the flow chart of FIG. 21.

Though the signal is a single ascending or descending transition, the minimum signal rise time considers the ascending and descending components that make up each signal. FIG. 23 illustrates how each ascending or descending signal has an opposite component. Both the actual signal and its opposite component are used (individually) to determine whether the signal has exceeded the minimum and maximum rise times.

The predictive waveform morphology sub-algorithm 406 may then classify all signals within a waveform based on minimum and maximum signal amplitude (step 432). The signal amplitude is the amplitude value change between the positive and negative peaks of a signal. (FIG. 24) The minimum signal amplitude is the amplitude required to qualify a given signal to be considered for marker placement. The maximum signal amplitude is the maximum amplitude value a signal can be to be considered for marker placement.

The predictive waveform morphology sub-algorithm 406 may then classify all signals based on the signal to noise ratio (step 434). The Signal to Noise Ratio (SNR) is calculated by taking the amplitude of the signal and dividing it by the calculated noise of the waveform. The minimum SNR defines the minimum SNR required to qualify a given signal to be considered for marker placement.

Figure 25:
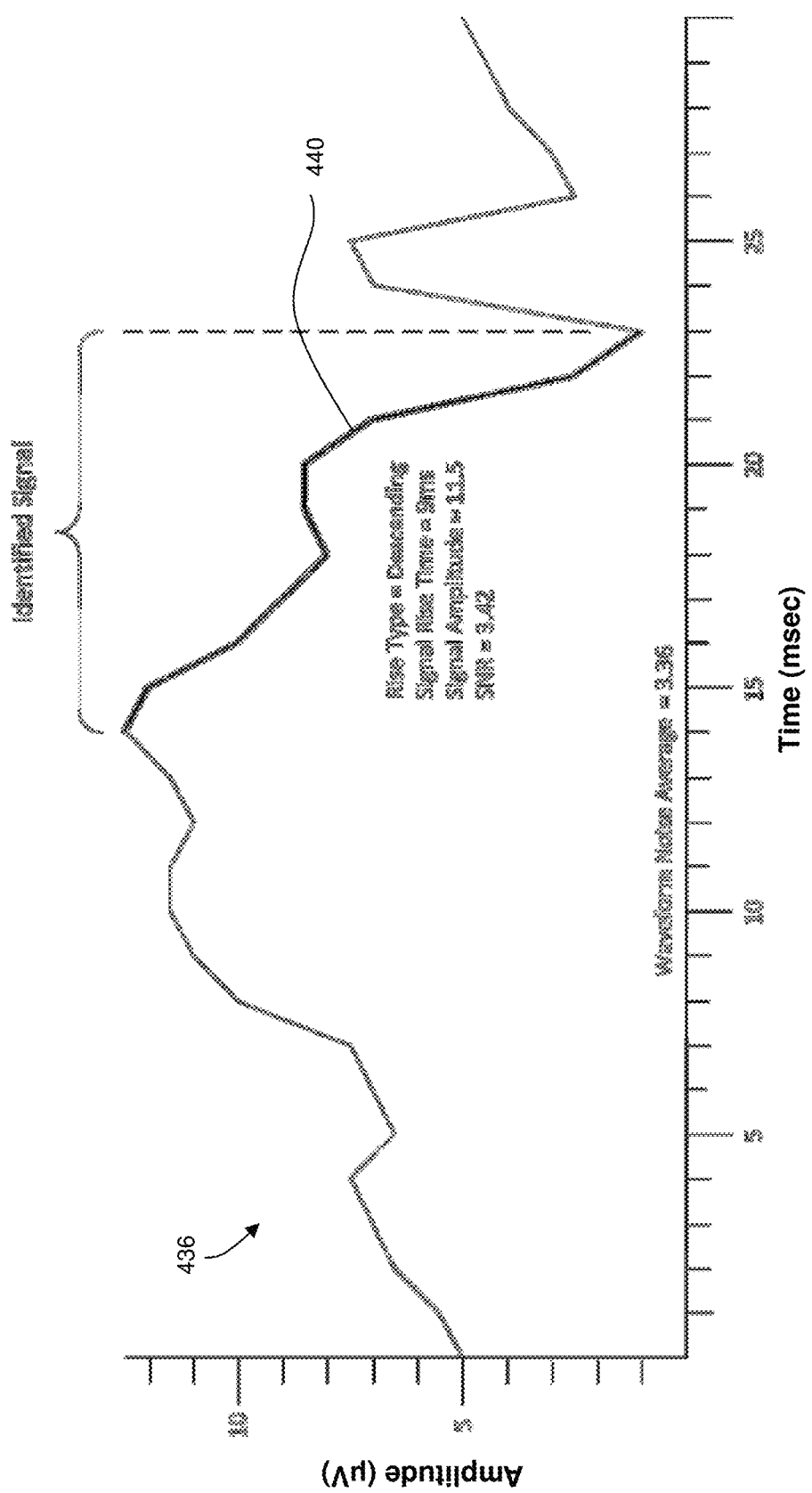
FIG. 25 depicts a signal identified as a potential physiologic signal following completion of the predictive waveform morphology search steps of the flow chart of FIG. 21.
Figure 26:
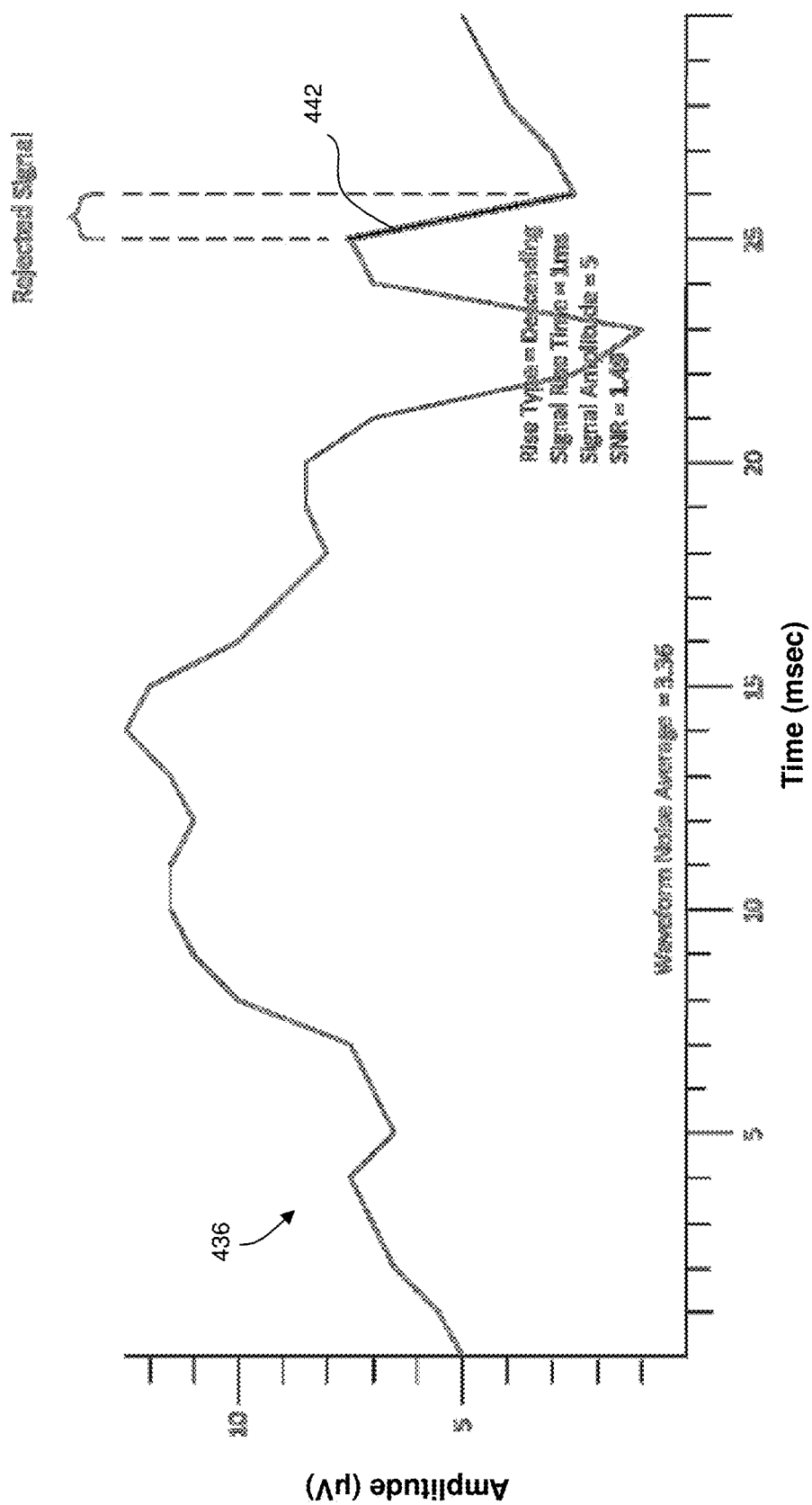
FIG. 26 depicts a signal excluded as a potential physiologic signal following completion of the predictive waveform morphology search steps of the flow chart of FIG. 21.

Thus, the identification and rejection of signal to be classified as a valid neurophysiologic signal can be made utilizing a set of predictive morphology search parameters. FIGS. 25 and 26 show an identified valid neurophysiologic signal (response) 440 and a rejected signal 442, respectively, based on the example predictive morphology search parameters of Table 3:

TABLE 3

| Parameter | Value |
| --- | --- |
| Signal rise type | Descending |
| Minimum signal rise time | 1.5 msec |
| Maximum signal rise time | 15.0 msec |
| Minimum signal amplitude | 0.5 µA |
| Maximum signal amplitude | 10.0 µA |
| Minimum SNR | 2.2 |

Specifically, the waveform of FIG. 25 is a descending signal segment with a rise time of 9 msec, signal amplitude of 11.5 µV, and a signal to noise ratio of 3.42. each of these values meet the parameters set forth in Table 3, so the identified signal 440 qualifies as a valid neurophysiologic signal and a candidate for marker placement in the waveform marker placement sub-algorithm 408 as will be discussed in greater detail below. The waveform of FIG. 26 is a descending signal segment of a signal rise time of 1 msec, signal amplitude of 5 µV, and a signal to noise ratio of 1.49. Because the minimum signal rise time and the signal to noise ratio in this example are lower than that required by the parameters of Table 3, the signal 442 will be rejected and will not be processed further at step 408.

Waveform Marker Location Search

With the signals processed and valid neurophysiologic signals identified as set forth above, the location of where to place waveform markers on the neurophysiologic signal may commence. FIGS. 27-31 depict the waveform marker location sub-algorithm 408 according to one embodiment. The waveform marker location sub-algorithm 408 applies search window criteria to determine which aspect of a signal that is most likely to be the neurophysiologic response. According to one embodiment, for determining the likely signal, the algorithm will search through a predefined number of signal candidates and determine which one is the largest. For example, if the search value is five, the algorithm will search through the first five signal candidates and determine which has the largest amplitude change. If there are less than five signal candidates, the algorithm will search through all of the candidates to determine the likely signal. It is contemplated that the algorithm possesses a plurality of search types that are variable and configurable.

Figure 27:
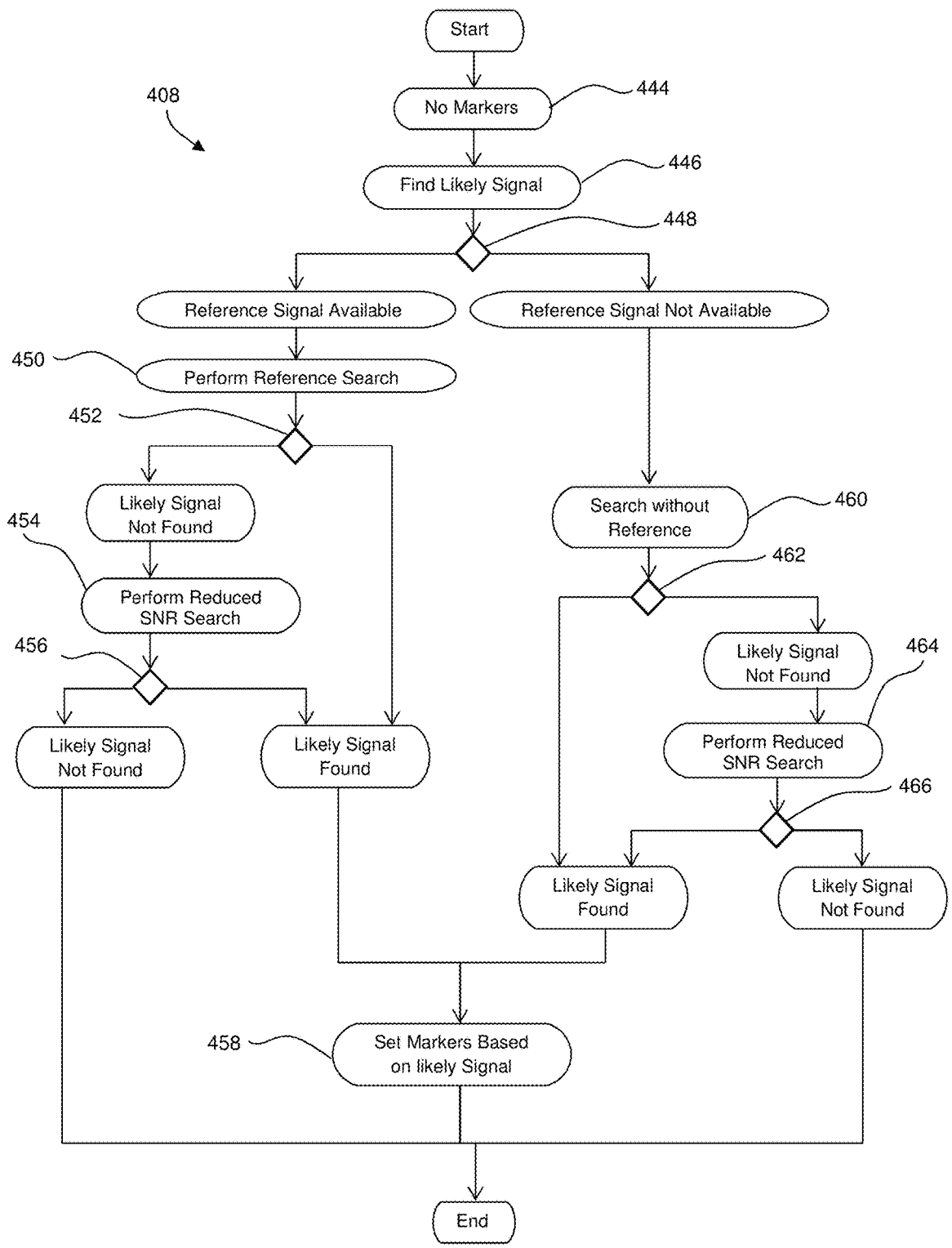
FIG. 27 is a flow chart detailing the steps of the marker location search portion of the algorithm of FIG. 13.

FIG. 27 is a flowchart depicting the steps of the waveform marker location sub-algorithm 408 in greater detail. At step 444, a waveform containing an identified signal from step 436 (above) but possessing no waveform identification markers is entered into the sub-algorithm processor. At step 446, a search is performed to find a likely neurophysiologic response signal based on whether or not a reference signal (or "baseline") is available. Next, the algorithm searches to ascertain whether a reference signal is available to compare it to (step 448).

Figure 28:
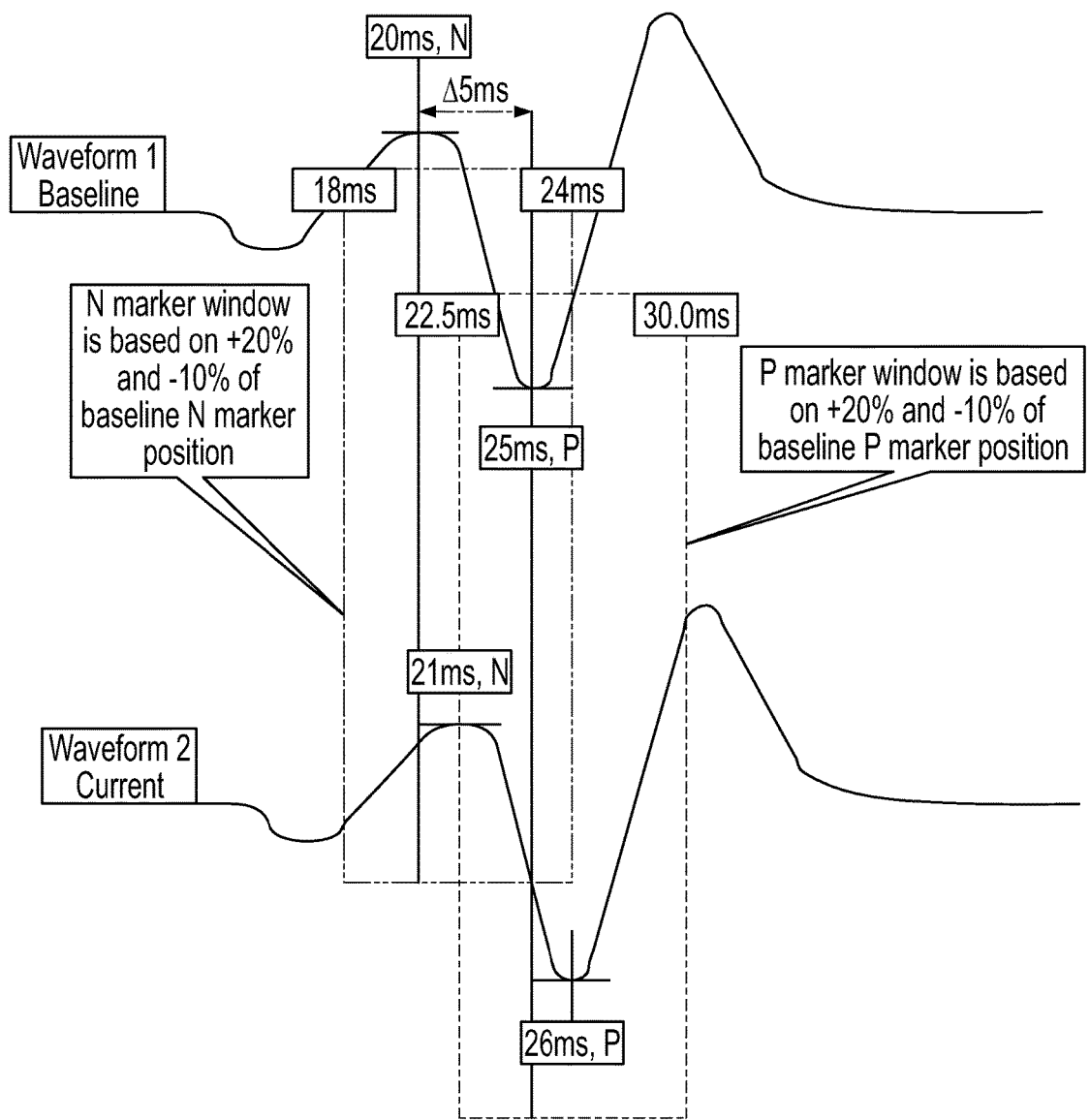
FIG. 28 depicts the marker placement on a likely physiologic signal based on a reference search as detailed in the flow chart of FIG. 27.

If a reference signal is available, a reference search is performed at step 450. According to one embodiment, if a reference signal is found at step 452, that reference signal's marker placement values can be used to create a targeted search window based on configurable parameters. By way of the example in FIG. 28, waveform 1 (baseline waveform) had latency markers placed at 20 msec and 25 msec. Using this as a reference, the search windows for waveform 2 (current waveform) are 18-24 msec and 22.5-30 msec based on a +20% and -10% reference window. Note that these are examples and in any implementation, the actual reference search window parameters can be variable. As can be seen in FIG. 28, a likely signal is found within this reference window. Next, markers may be set based on this likely signal at step 458 as will be discussed below. One of skill in the art will readily appreciate that performing a reference search of this type allows the identified signals in the current waveform to be processed much more quickly as signals that start or end outside of the reference window are ignored.

The reference search may also take into account the signal rise type of the marked signal of the baseline when searching. By way of illustration, if the reference's marked signal is descending, then the reference search will only qualify descending signals as valid. With SSEP, the algorithm uses a predictive morphology (a descending cortical signal for instance) to search. However, if the user decides to mark an ascending signal instead of the predicted descending signal as in the prior example, the reference will "learn" from the user's actions and search for an ascending signal to match that of the signal marked on the baseline according to one embodiment.

Figure 29:
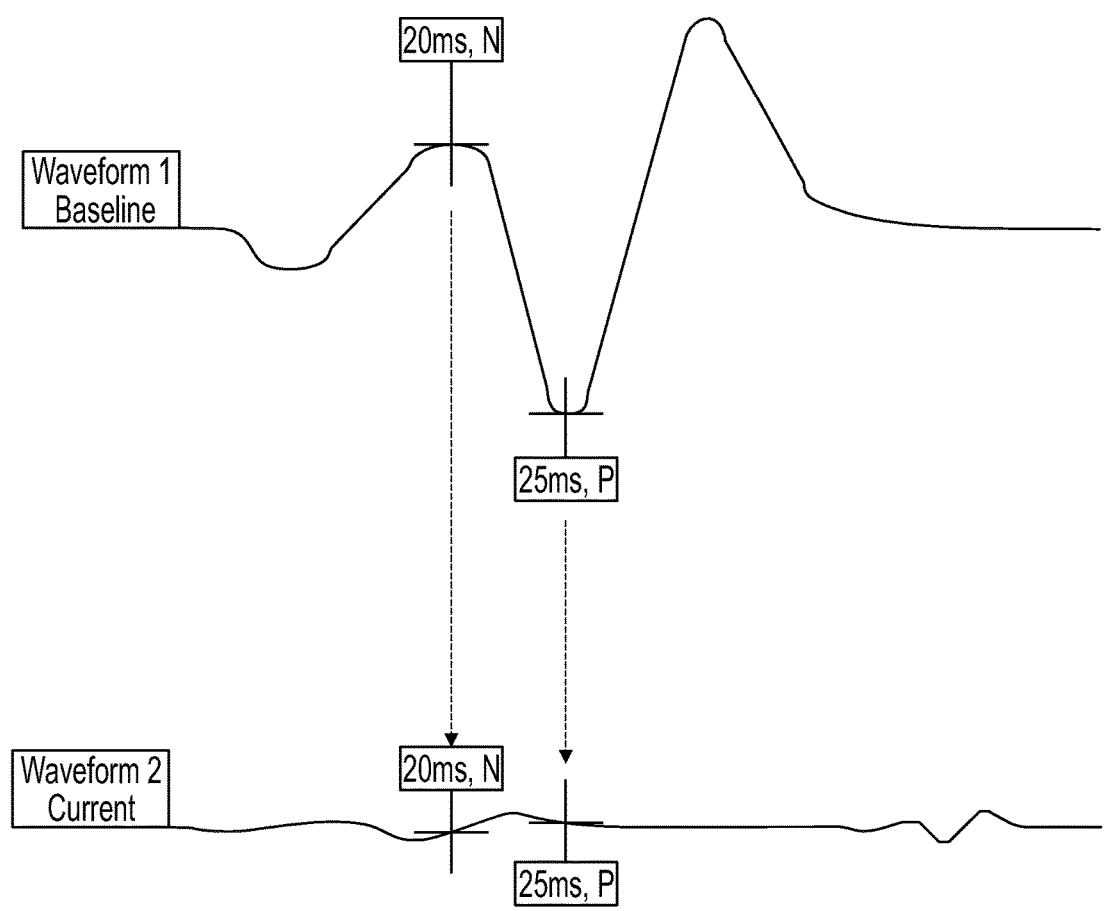
FIG. 29 depicts the marker placement on a waveform in which a likely physiologic signal was not found based on a reference search as detailed in the flow chart of FIG. 27.
Figure 30:
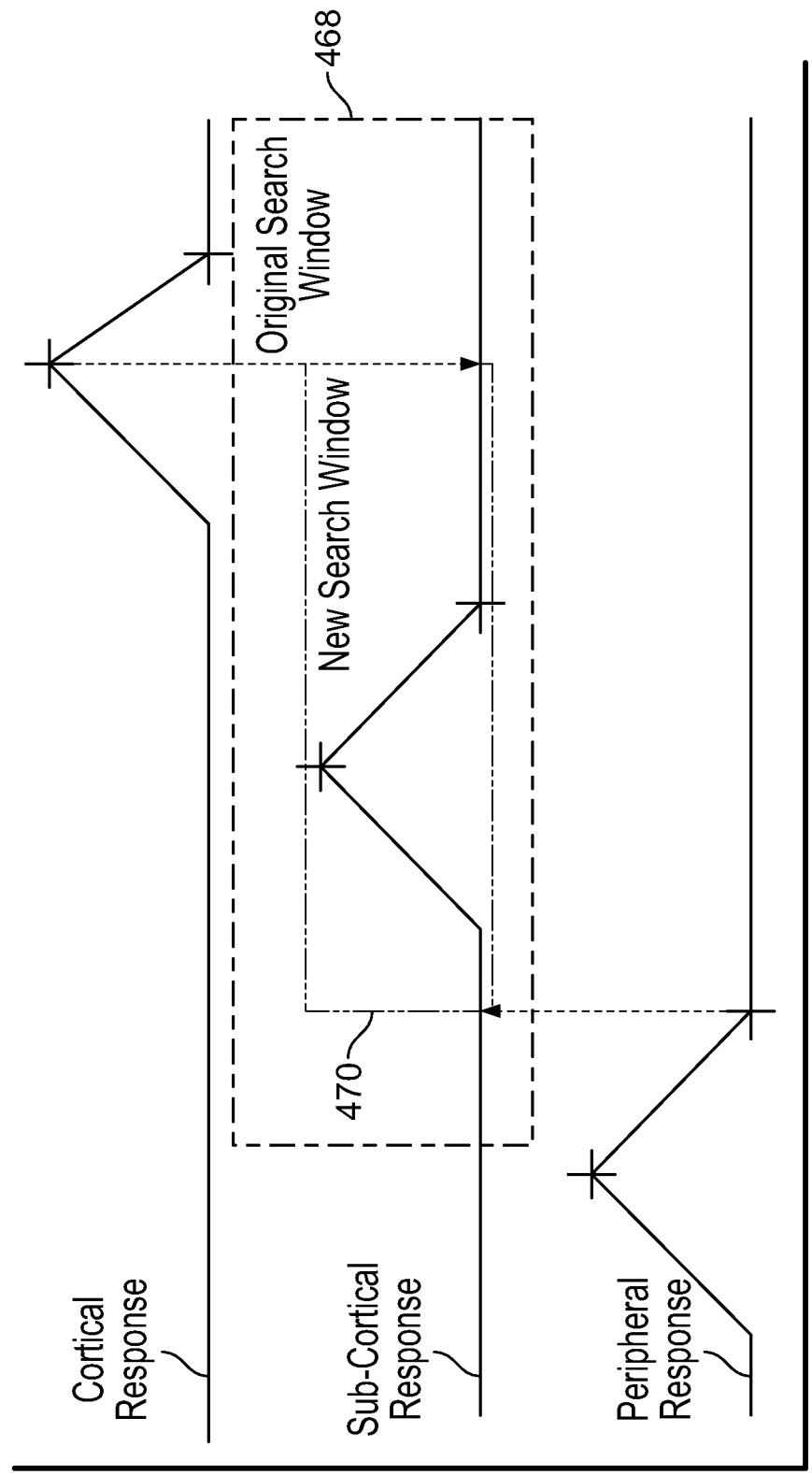
FIG. 30 shows narrowing of the original search windows via the comparative search placement function.

When searching for the likely response signal within a waveform, the algorithm attempts to locate a signal that exceeds the noise level by a predefined value (a SNR value of 2.2, for example.). As depicted in the flowchart of FIG. 27, if a likely signal is not found at step 452, a second pass is performed using a slightly lower SNR value (step 454). For example, if the first pass fails to find a likelysignal at an SNR of 2.2, a second pass will look for a signal at an SNR 10% lower than the original SNR (or 1.98). If a likely signal is found as a result of this second pass (step 456), markers will be set based on this likely signal (step 458). However, if a likely signal is not found as a result of this second pass (step 456) i.e., if a signal meeting the search criteria cannot be found matching the baseline), the marker latency values for the search (at step 458) will be the same as those for the original reference (baseline) signal by "dropping the amplitude value" from one recording into the next. FIG. 29 illustrates no valid, matching signal in waveform 2 (current waveform) when compared to waveform 1 (baseline/reference) so the markers are "dropped" to the same time-based locations on the waveform 2 as waveform 1.

Returning back to step 448, if it is determined that there is no reference signal available (perhaps because a baseline has yet to be established), the algorithm may search without a reference (step 460) using one or more search types. The first type of search executable by the algorithm 408 is a default window search which uses configurable parameters to define windows in which a valid neurophysiologic signal can be included. In one embodiment, the default window search provides a time-based window in which to search for the likely signal. The beginning and end of the window for each of the markers to be searched for can be configured based on clinical data. For example, a SSEP response comprises somewhat predictable negative and positive (N and P) latencies. These latency values can be bracketed by the beginning and end windows using the default window search. If a likely signal is found using the default reference search, the markers may be placed on that likely signal at step 466. However, if a likely signal is not found, a second pass is performed using a slightly lower SNR value (step 464). For example, if the first pass fails to find a signal at an SNR of 2.2, a second pass will look for a signal at an SNR 10% lower than the original SNR (or 1.98). If a likely signal is found as a result of this second pass, the algorithm will set markers based on this likely signal (step 466). However, if no likely signal is found, the algorithm may default and place the markers at 0 msec.

The results of the default window search can be further narrowed by optionally performing a comparative search. The comparative search capitalizes on the fact that waveforms can be related to one another and when they are, the algorithm 406 may search for the likely signal in each waveform in a pre-defined order using any likely signals found to further tighten the search windows of subsequent searches. According to one embodiment, the comparative search allows the algorithm to use the identified marker locations from associated waveforms to help narrow the default search window. By way of example only, with SSEPs, three recording channels often are used (e.g. a cortical channel, a subcortical channel, and a peripheral channel). The relationship between the waveforms of each of the three channels is that none of the marked responses overlap because the latencies for each is different: the peripheral channel having the shortest latency, the subcortical channel having an intermediate latency, and the cortical channel having the longest latency (see FIG. 30). Using this relationship, the algorithm can find one or two bounding waveform response signals and use them to determine a smaller search window for the third waveform response as will be explained in greater detail below.

Figure 31:
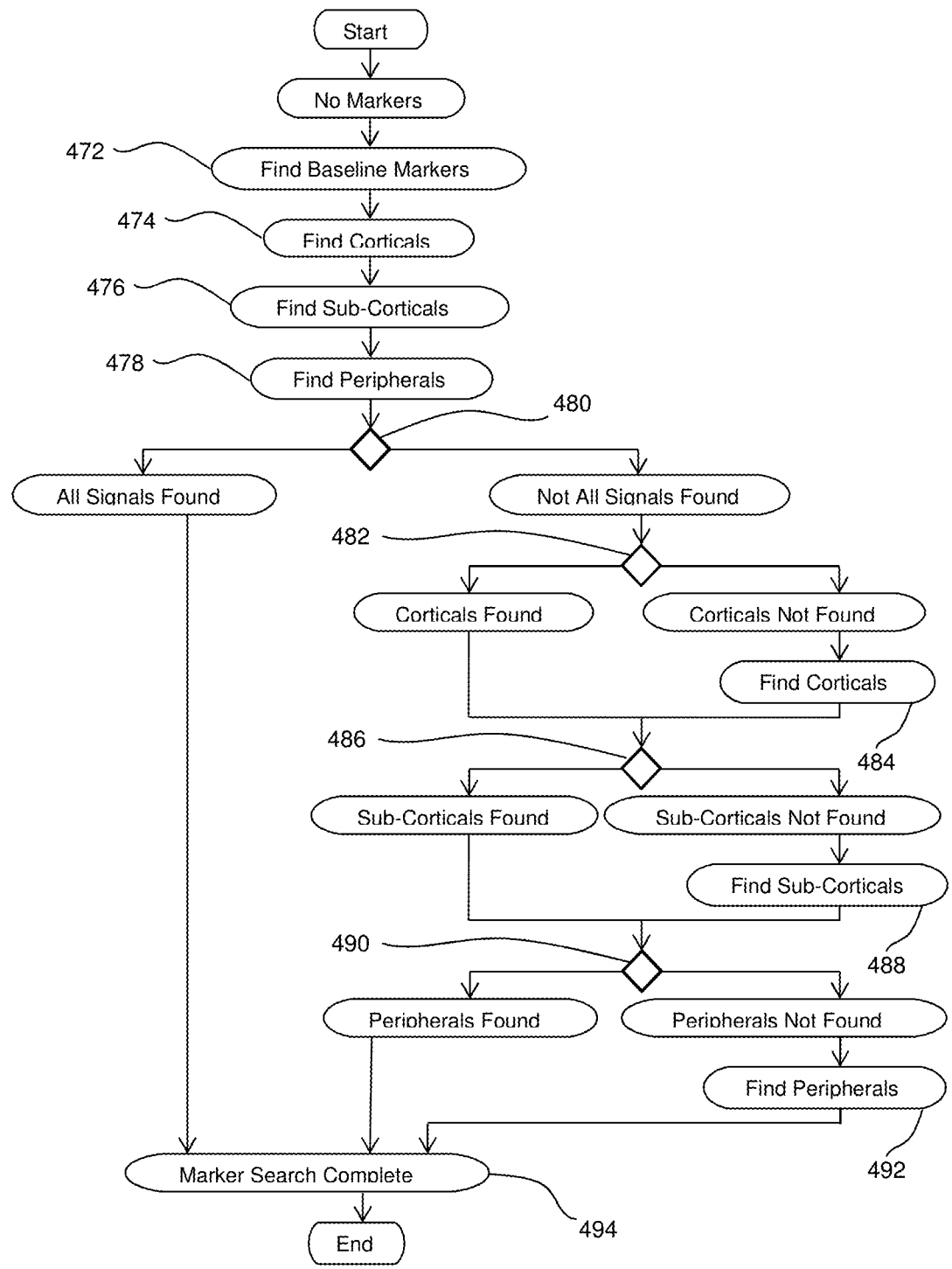
FIG. 31 is a flow chart detailing the steps of the comparative marker placement function.

FIG. 31 depicts a flowchart highlighting the steps of the comparative search function according to one embodiment. Step 472, a waveform containing an identified signal from step 436 (above) but possessing no waveform identification markers enters a first pass into the sub-algorithm processor. The algorithm first searches for cortical SSEP responses at step 474 and attempts to place cortical waveform markers if possible. At step 476, the algorithm will attempt to find the sub-cortical responses and place subcortical waveform markers and will incorporate the cortical marker latency values to represent an end boundary for the subcortical latency search window. At step 478, the algorithm will next attempt to find the peripheral responses and will incorporate either or both the cortical and sub-cortical marker latency values as an end boundary for the peripheral latency search window.

At step 480, the algorithm determines whether all cortical, sub-cortical, and peripheral response were found. If yes, the marker search will be deemed complete at step 494. If no, however, the algorithm proceeds to step 482 and performs a second pass using a reduced SNR search similar to that described above. Following the reduced SNR search, the algorithm will search for cortical responses (step 482). If a cortical response was found, the marker is placed, the algorithm proceeds to step 486. If no, the algorithm uses the sub-cortical and peripheral latency values to help narrow the cortical latency search window if possible (step 484). After the cortical signal has been processed, the algorithm proceeds to step 486 and will search for subcortical responses. If a subcortical response was found, the marker is placed and the algorithm proceeds to step 490. If no, the algorithm uses the cortical and peripheral latency values to help narrow the subcortical latency search window if possible 488. After the subcortical signal has been processed, the algorithm proceeds to step 490 and will search for peripheral responses. If a peripheral response was found, marker is placed and the algorithm proceeds to step 494. If no, the algorithm uses the cortical and subcortical latency values to help narrow the peripheral latency search window if possible. After the peripheral response has been processed, the marker search is complete 494. It is to be appreciated that the default window search and comparative search are preferably used to determine a baseline/reference response. From there, the reference search is preferably used throughout the rest of the surgical procedure to automatically place waveform markers.

While this invention has been described in terms of a best mode for achieving this invention's objectives, it will be appreciated by those skilled in the art that variations may be accomplished in view of these teachings without deviating from the spirit or scope of the present invention. For example, the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present invention is not limited by the specified scope.

What is claimed is:

1. A method of performing neuromonitoring of a patient during a surgical procedure, said method comprising the steps of:

obtaining a raw waveform ready for processing, wherein said raw waveform is comprised of electrical response signals recorded by recording electrode resulting from a neuromonitoring stimulus provided to the patient wherein said neuromonitoring stimulus is initiated by a processing unit and delivered to a stimulus electrode via a stimulation source, wherein said electrical response signal is delivered to a recording channel, wherein said recording channel sends said electrical response signal to the processing unit, wherein said electrical response signals are comprised of valid neurophysiologic response signal components and invalid neurophysiologic response signal components;

generating a derived processed waveform by the processing unit comprised of a first set of potentially valid neurophysiologic response signal components within the raw waveform, wherein said derived processed waveform excludes a first set of invalid neurophysiologic response signal components within the raw waveform, wherein said derived processed waveform generated by the processing unit excludes noise components from the raw waveform and is generated by the processing unit from ascending peaks and descending peaks of the raw waveform, and wherein said first set of the potentially valid neurophysiologic response signal components is stored in a storage device;

identifying a second set of potentially valid neurophysiologic response signal components by said processing unit in the derived processed waveform, wherein the second set of potentially valid neurophysiologic response signal components is a subset of the first set of potentially valid neurophysiologic response signal components, by rejecting the signal components of the first set of potentially valid neurophysiologic response signal components that do not meet predetermined signal morphology criteria, wherein said predetermined signal morphology criteria is at least one of minimum signal rise time, maximum signal rise time, minimum signal amplitude, maximum signal amplitude, and minimum signal to noise ratio, and wherein said second set of potentially valid neurophysiologic response signal components is stored in said storage device;

searching the second set of potentially valid neurophysiologic response signal components by said processing unit to determine said valid neurophysiologic response signal components, wherein said valid neurophysiologic response signal components are determined based on the second set of potentially valid neurophysiologic response signal components that exceed the signal to noise ratio level by a predefined value;

displaying latency and amplitude marker locations on said raw waveform by said processing unit based on the location of said valid neurophysiologic response signal components, said latency and amplitude marker locations having an associated value;

measuring the value, at one of said marker locations, of at least one waveform characteristic, by said processing unit wherein said waveform characteristic is at least one of amplitude and latency;

comparing the value of said at least one measured waveform characteristic with a value of a baseline waveform characteristic to determine a difference between the values by said processing unit;

issuing a warning if the difference between the value of said at least one measured waveform characteristic and the value of the baseline waveform characteristic increases or decreases by a predetermined level by said processing unit.

2. The method of claim 1, wherein the generating a derived processed waveform further comprises the processing unit iteratively identifying negative and positive peaks in said raw waveform.

3. The method of claim 1, wherein the generating a derived processed waveform step by the processing unit further comprises the steps of:
  (a) determining the value of the ascending peaks, the descending peaks, and the noise of the raw waveform;
  (b) generating a derived average waveform based on the ascending peaks, the descending peaks, and the noise of the raw waveform, wherein said derived average waveform has ascending peaks and descending peaks;
  (c) determining the value of the ascending peaks and the descending peaks of the derived average waveform; and
  (d) comparing the values of the ascending peaks and the descending peaks of the raw waveform to the values of the ascending peaks and the descending peaks of the derived average waveform to generate the derived processed waveform.

4. The method of claim 1, wherein the step of identifying the second set of potentially valid neurophysiologic response signal components in the derived processed waveform comprises the processing unit rejecting the signal components of the first set of potentially valid neurophysiologic response signal components that do not meet at least two of minimum signal rise time, maximum signal rise time, minimum signal amplitude, maximum signal amplitude, and minimum signal to noise ratio.

5. The method of claim 1, wherein the step of identifying the second set of potentially valid neurophysiologic response signal components in the derived processed waveform comprises the processing unit rejecting the signal components of the first set of potentially valid neurophysiologic response signal components that do not meet at least four of minimum signal rise time, maximum signal rise time, minimum signal amplitude, maximum signal amplitude, and minimum signal to noise ratio.

6. The method of claim 1, wherein the searching step further comprises the processing unit using a reference signal having latency markers at designated times to develop a time period search window for searching the second set of potentially valid neurophysiologic response signal components.

7. The method of claim 1, further comprising the processing unit finding directional changes in said raw waveform.

8. The method of claim 1, further comprising the processing unit identifying noise spikes and calculating a noise level for said raw waveform.

9. The method of claim 1, further comprising the processing unit excluding an early latency portion of said raw waveform from a noise calculation to disqualify any stimulus artifact present at an onset of said raw waveform from entering into the noise calculation.

10. A system for providing neuromonitoring of a patient during a surgical procedure, comprising:
  a control unit comprised of a main display and a processing unit,
  a stimulation source,
  a storage device, and
  an electrode harness, wherein the control unit is configured to:
    activate a stimulation signal in the electrode harness via the stimulation source;
    receive a waveform from the patient recorded by the electrode harness, wherein the waveform is an electrical response signal, and in response to the stimulation signal, wherein said electrical response signal is comprised of valid neurophysiologic response signal components and invalid neurophysiologic response signal components;
    identify a first set of potentially valid neurophysiologic response signal components within the waveform by said proceeding unit, wherein the processing unit processes said first set of potentially valid neurophysiologic response signal components to exclude a first set of invalid neurophysiologic response signal components of the waveform, wherein said first set of invalid neurophysiologic response signal components are excluded based on noise components and the ascending peaks and descending peaks of the waveform, and wherein said first set of potentially valid neurophysiologic response signal components are stored in the storage device;
    perform a predictive waveform morphology search on the waveform by said processing unit to identify a second set of potentially valid neurophysiologic response signal components in the first set of potentially valid neurophysiologic response signal components that match neurophysiologic waveform morphology criteria and rejecting the signal components of the first set of potentially valid neurophysiologic response signal components that do not match neurophysiologic waveform morphology criteria, wherein said neurophysiologic waveform morphology criteria is at least one of minimum signal rise time, maximum signal rise time, minimum signal amplitude, maximum signal amplitude, and minimum signal to noise ratio, and wherein the second set of potentially valid neurophysiologic response signal components is a subset of the first set of potentially valid neurophysiologic response signal components;

search the second set of potentially valid neurophysiologic response signal components by said processing unit to determine said valid neurophysiologic response signals, wherein said valid neurophysiologic response signals are determined based on the second set of potentially valid neurophysiologic response signal components that exceed the signal to noise ratio level by a predefined value, and wherein said second set of potentially valid neurophysiologic response signal components are stored in the storage device;

determine the location where markers should be placed on the waveform by said processing unit based on the location of said valid neurophysiologic response signals within the waveform, wherein said determined marker location has an associated value;

place markers on the waveform by said processing unit;

compare the determined marker location value with a baseline waveform marker location value to determine a difference between the values by said processing unit; and issue a warning if the difference between the determined marker location value and the baseline waveform marker location value increases or decreases by a predetermined level by the main display.

11. The system of claim 10, wherein the processing unit is further configured to calculate a noise level for the waveform.

12. The system of claim 10, wherein the waveform morphology criteria is at least three of signal rise type, signal rise time, signal amplitude and signal to noise ratio.

13. The system of claim 10, wherein, when a reference signal is available, the processing unit is further configured to:
   create at least one target window search based on marker placement values in the reference signal; and
   wherein the searching step searches the second set of potentially valid neurophysiologic response signal components in the at least one target window.

14. The system of claim 13, wherein, when a reference signal is not available, the processing unit is further configured to:
   search, in the searching step, the second set of potentially valid neurophysiologic response signal components in a default window.

15. The system of claim 14, wherein the processing unit is further configured to:
   narrow the default window by using marker locations from other waveforms of the patient.

* * * * *

UNITED STATES PATENT AND TRADEMARK OFFICE
CERTIFICATE OF CORRECTION

PATENT NO. : 9,757,072 B1
APPLICATION NO. : 14/178176
DATED : September 12, 2017
INVENTOR(S) : Edward C Urbalejo Page 1 of 1

It is certified that error appears in the above-identified patent and that said Letters Patent is hereby corrected as shown below:

On the Title Page

- In the Inventor (72), please delete "Edward C Urbalejo" and insert --Edward S Urbalejo--, therefor.

Signed and Sealed this
Sixteenth Day of April, 2019

Andrei Iancu
*Director of the United States Patent and Trademark Office*